United States Patent [19]

Chu et al.

[11] Patent Number: 5,262,400
[45] Date of Patent: Nov. 16, 1993

[54] 4α-SUBSTITUTED AVERMECTIN DERIVATIVES

[75] Inventors: Lin Chu, Waldwick; Helmut Mrozik, Matawan; Todd K. Jones, Edison, all of N.J.

[73] Assignee: Merck & Co., Inc., Rahway, N.J.

[21] Appl. No.: 882,809

[22] Filed: May 19, 1992

Related U.S. Application Data

[63] Continuation-in-part of Ser. No. 810,999, Dec. 20, 1991, abandoned, which is a continuation-in-part of Ser. No. 717,953, Jun. 20, 1991, abandoned.

[51] Int. Cl.$^5$ .................... A61K 31/70; A61K 31/365
[52] U.S. Cl. ...................................... 514/30; 514/450;
536/7.1; 549/264
[58] Field of Search .................. 514/30, 450; 549/264; 536/7.1

[56] References Cited

U.S. PATENT DOCUMENTS

| | | | |
|---|---|---|---|
| 3,950,360 | 4/1976 | Aoki et al. | 549/264 |
| 4,171,314 | 10/1979 | Chabala et al. | 536/7.1 |
| 4,206,205 | 6/1980 | Mrozik et al. | 548/264 |
| 4,310,519 | 1/1982 | Albers-Schonberg et al. | 536/7.1 |
| 4,457,920 | 7/1984 | Mrozik et al. | 549/264 |

FOREIGN PATENT DOCUMENTS

| | | |
|---|---|---|
| 170006 | 2/1986 | European Pat. Off. . |
| 237341 | 9/1987 | European Pat. Off. . |
| 303933 | 8/1988 | European Pat. Off. . |
| 02017181 | 1/1990 | Japan . |
| 2166436 | 5/1986 | United Kingdom . |

OTHER PUBLICATIONS

Albers-Schonberg, et al (II) J. Am. Soc. 103 pp. 4216-4221 (1981).
Chabala, et al (III) J. Med. Chem. 23 pp. 1134-1136 (1980).
Carter, et al J. Antibiotics 41 pp. 519-529 (1988).
Danishefsky, et al J. Am. Chem. Soc. 111 (1989) pp. 2967-2980.
Hanessien, et al. (I) J. Am. Chem. Soc. 109 (1987) pp. 7063-7067.
Fraser-Reid, et al J. Am. Chem. Soc. 109 (1987) pp. 933-935.
Derwent Abstract, 90-063696/09.

*Primary Examiner*—C. Warren Ivy
*Assistant Examiner*—A. Owens
*Attorney, Agent, or Firm*—David L. Rose; Joseph F. DiPrima

[57] ABSTRACT

Avermectin compounds are substituted at the 4a-position: the 4a-methyl group is first derivatized with a hydroxy group which is then substituted with a variety of alkyl, alkoxy alkyl, or polyalkoxy alkyl groups and derivatives thereof. The compounds are potent antiparasitic and anthelmintic agents and compositions for such uses are also disclosed.

13 Claims, No Drawings

4a-SUBSTITUTED AVERMECTIN DERIVATIVES

CROSS REFERENCE TO RELATED APPLICATIONS

This application is a continuation-in-part of our application Ser. No. 810,999 filed Dec. 20, 1991, which is a continuation-in-part of application Ser. No. 717,953 filed Jun. 20, 1991, both now abandoned.

BACKGROUND OF THE INVENTION

The avermectins (previously referred to as C-076 compounds) are a series of compounds produced by fermentation of avermectin producing strains of Streptomyces avermitilis and derivatives thereof. The morphological characteristics of the culture are completely described in U.S. Pat. No. 4,310,519. The production, isolation, and structure determination of the avermectins are fully described in Albers-Schonberg et al *J. Am. Chem. Soc.* 1981, 103, 4216–4221 and references cited therein. The conversion of natural avermectin $B_1$ to 22,23-dihydro-avermectin $B_1$, the potent broad spectrum anthelmintic agent known as ivermectin, has also been described in the literature (Chabala et al *J. Med. Chem.* 1980, 23, 1134–1136). The naturally occurring avermectins and the instant derivatives thereof have a very high degree of anthelmintic and anti-parasitic activity.

The naturally occurring avermectins are a series of macrocyclic lactones which are substituted at position 13 with a disaccharide consisting of two oleandrose residues. The natural compounds have the following general structure:

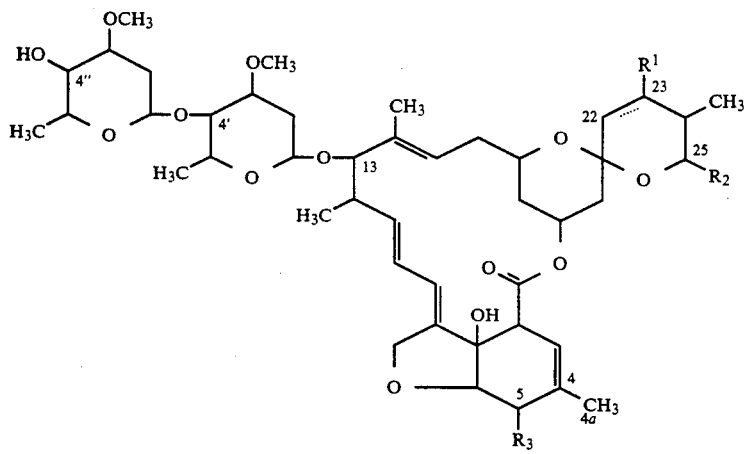

wherein the broken line indicates a single or double bond at the 22,23-position and;

$R_1$ is hydroxy and is present only when said broken line indicates a single bond;

$R_2$ is iso-propyl or sec-butyl; and $R_3$ is methoxy or hydroxy.

There are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | broken line | $R_1$ | $R_2$ | $R_3$ |
|---|---|---|---|---|
| A1a | 22,23-double bond | — — | sec-butyl | —OCH₃ |
| A1b | 22,23-double bond | — — | iso-propyl | —OCH₃ |
| A2a | 22,23-single bond | —OH | sec-butyl | —OCH₃ |
| A2b | 22,23-single bond | —OH | iso-propyl | —OCH₃ |
| B1a | 22,23-double bond | — — | sec-butyl | —OH |
| B1b | 22,23-double bond | — — | iso-propyl | —OH |
| B2a | 22,23-single bond | —OH | sec-butyl | —OH |
| B2b | 22,23-single bond | —OH | iso-propyl | —OH |

The avermectins are generally isolated as mixtures of the a and b components (typically ≧80% a and ≦20% b). Such compounds differ only in the nature of the $R_2$ substitutent and this minor structural difference has been found to have very little effect on the chemical reactivity or biological activity of the compounds. Thus although the a and b components can be separated from each other by chromatography this is not necessary and hence is not normally done. The presence of a mixture of a and b components is indicated by dropping the a or b from the designation of the compound. A mixture of avermectin B1a and avermectin B1b is thus referred to as avermectin B1.

A related family of natural products is known as the milbemycins. The milbemycins have the same basic structure as the avermectins but have no substitution at position 13 and have a methyl or ethyl group at position 25 ($R_2$=methyl or ethyl rather than isopropyl or sec-butyl as in the avermectins). The milbemycins and the fermentation conditions used to prepare them are described in U.S. Pat. No. 3,950,360. Closely related 13-deoxy-avermectin aglycones are prepared by chemical modification of the natural avermectins and have been described in U.S. Pat. Nos. 4,171,134 and 4,173,571. Avermectin aglycones, which may also be used as starting material for the instant compounds are disclosed in U.S. Pat. No. 4,206,205. U.S. Pat. No. 4,457,920 described 4a-derivatives of avermectin compounds in which the 4a-substitutents are hydroxy, acetyloxy, benzoyloxy, pyridinyl carbonyloxy, pyrrolyl carbonyloxy or carboxyethanoyloxy. This reference also discloses the preparation of the 4a-hydroxy compounds which are the starting materials for the instant compounds.

Japanese patent publication 02,017,191 also describes compounds with 4a-substituents. The 4a-substitutents disclosed include azido, halo, cyano, alkanoyloxy, alkoxy, and nitrogen and sulfur substituted derivatives.

Recently a number of related compounds have been described in European Patent Application EPO 170,006 and U.K. aplication 2,166,436 (see also Carter et al., *J. Antibiotics* 1988, 41, 519–529). These compounds are essentially 13-deoxy-avermectin aglycones in which the $R_2$ side chain contains a double bond and, in some cases, includes additional carbon atoms.

Chemically modified derivatives of this group of compounds have recently become known. In particular compounds containing a N-methoxyimino substituent attached to the C-23 position are described in UK Patent Application GB 2 192 630 A and European Patent Application 0 237 341 A1. Moxidectin is the generic name for a compound of this group with the chemical name [6R, 25S(E)]-5-0-demethyl-28-deoxy-25-(1,3-dimethyl-1-butenyl)-6,28-epoxy-23-(methoximino) Milbemycin B.

Recent publications have described the synthesis of avermectin A1a (Danishefsky et al, *J. Am. Chem. Soc.* 1989, 111, 2967) and avermectin B1a (Hanessian et al, *J. Am. Chem. Soc.* 1986, 108, 2776). Research on deconjugation and epimerization of avermectin C-2 stereoisomers is described in the two synthetic publications cited above as well as in Hanessian et al (*J. Am. Chem. Soc.* 1987, 109, 7063) and Fraser-Reid et al (*J. Am. Chem. Soc.* 1987, 109, 933).

The avermectins are highly potent anthelminthic and antiparasitic agents and are relatively non-toxic to most mammalian species. However, the avermectins are highly toxic to certain mammalian species and this fact precludes the use of avermectins for some applications. In addition, the avermectins are ineffective against some parasites and resistant strains of previously susceptible parasites may evolve. Thus it is desirable to discover novel avermectin analogs with improved activity and/or lower mammalian toxicity.

SUMMARY OF THE INVENTION

The instant invention is concerned with avermectin compounds which are substituted at the 4a-position by a variety of oxygen containing substituents in which the substituent is connected to the 4a-methyl group through the oxygen atom. Thus, it is an object of this invention to described such 4a-substituted compounds. It is a further object to described the procedures for the preparation of such compounds. A still further object is to describe the use of such compounds as antiparasitic and anthelmintic agents. A still further objective is to describe compositions containing such compounds for use as antiparasitic and anthelmintic agents. Still further objects will become apparent from a reading of the following description.

DESCRIPTION OF THE INVENTION

The compounds of the instant invention are best realized in the following structural formula.

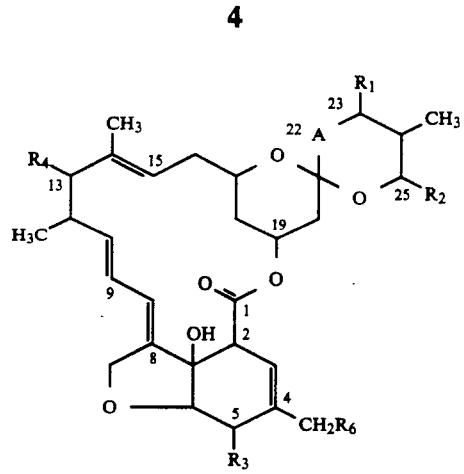

where
A is a 22,23 single bond or a double bond;
$R_1$ is hydrogen, hydroxy, oxo, oximino or methoxyimino provided that $R_1$ is present only when A is a single bond;
$R_2$ is $C_1$–$C_8$ alkyl, or $C_2$–$C_8$ alkenyl or a $C_3$–$C_8$ cycloalkyl;
$R_3$ is hydroxy, methoxy, oxo or hydroximino;
$R_4$ is hydrogen, halogen, hydroxy, $(C_1$–$C_8$ alkoxy$)_n$ where n is 1 to 4,

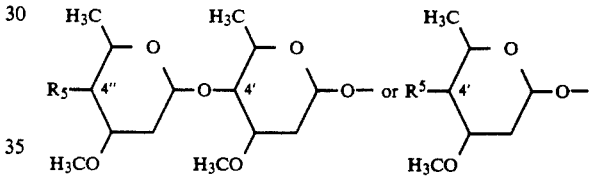

where $R_5$ is hydroxy, oxo, amino, $C_1$–$C_8$ mono-or dialkyl amino, $C_1$–$C_8$-alkanoyl amino, N-$C_1$–$C_8$ alkyl-N-$C_1$–$C_8$ alkanoyl amino, $(C_1$–$C_8$ alkoxy$)_n$ where n is 1 to 4, $C_1$–$C_8$ alkylthio, $C_1$–$C_8$ alkylsulfinyl, $C_1$–$C_8$ alkylsulfonyl or morpholinylcarbonyl hydrazonyl; and
$R_6$ is hydroxy, $C_1$–$C_8$ alkanoyloxy, benzoyloxy, di-$C_1$–$C_8$ alkylaminobenzoyloxy, pyrrolocarbonyloxy, nicotinoyloxy, $(C_1$–$C_8$ alkoxy$)_n$ where n is 1–4, $C_1$–$C_8$ alkylthio, tetrahydropyranyloxy, $C_1$–$C_8$ alkylthio —$C_1$–$C_8$ alkoxy or oleandrosyloxy provided that $R_6$ is hydroxy, $C_1$–$C_8$ alkanoyloxy, benzoyloxy, pyrrolocarbonyloxy or nicotinoyloxy only when $R_5$ is other than hydroxy or $R_4$ is other than hydrogen.

Above structural formula is shown without a definitive sterochemistry. However, during the course of the synthetic procedures used to prepare such compounds, the products of such procedures can be a mixture of stereoisomers. In particular, the substituents of the stereoisomers at the 4"-,4'-,13-,23-,24-, and 25-positions may be oriented either α or β- representing such groups being below or above the general plane of the molecule, respectively. In each such case both the α- and β-configurations are intended to be included within the ambit of this invention. In certain cases the term "epi" is used to distinguish the stereoisomer being of opposite configuration to the natural compound at one specific asymmetrical carbon atom.

Preferred compounds as realized in the foregoing structural formula where:
A is a 22,23-single bond or a double bond and $R_1$ is hydrogen;

$R_2$ is $C_3$–$C_6$ alkyl or $C_5$–$C_6$ cycloalkyl;
$R_3$ is hydroxy or hydroximino;
$R_4$ is hydroxy, $(C_1$–$C_4$ alkoxy$)_n$ where n is 1 to 3, or

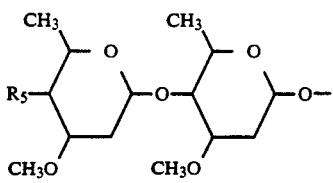

where $R_5$ is hydroxy, $C_2$–$C_4$ alkanoyl amino, N-$C_1$–$C_4$-alkyl-N-$C_1$–$C_4$ alkanoyl amino, $(C_1$–$C_4$ alkoxy$)_n$ where n is 1 to 4 or morpholinyl carbonyl hydrazonyl; and $R_6$ is hydroxy, $C_2$–$C_4$ alkanoyloxy, benzyoyloxy, nictinoyloxy or $(C_1$–$C_4$ alkoxy$)_n$ where n is 1–4.

Further preferred compounds are realized in the above formula when:

A is a 22,23-single bond or double bond and $R_1$ is hydrogen;

$R_2$ is $C_3$–$C_6$ branched alkyl or $C_6$ cycloalkyl;
$R_3$ is hydroxy;

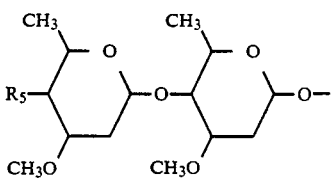

where
$R_5$ is $C_2$–$C_4$ alkanoyl amino or N-$C_1$–$C_2$ alkyl-N-$C_2$–$C_3$ alkanyolamino; and $R_6$ is hydroxy, acetoxy, benzoyloxy, nicotinoyloxy, or $(C_1$–$C_2$ alkoxy$)_n$ where n is 1–3.

The most preferred compounds of this invention are realized in the above structure when:

A is a 22,23-single bond or double bond and $R_1$ is hydrogen;
$R_2$ is isopropyl or sec-butyl;
$R_3$ is hydroxy;
$R_4$ is

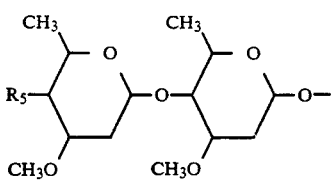

where
$R_5$ is N-acetyl amino or N-methyl-N-acetyl amino; and $R_6$ is hydroxy, acetoxy, benzoyloxy, nicotinoyloxy, or methoxy ethoxy methoxy.

It is to be noted that in the foregoing definitions the polyalkoxy group, written as $(C_1$–$C_8$-alkoxy$)_n$, the various alkoxy groups need not all be of the same length or configuration of carbon chains.

Some examples of specific preferred compounds of this inventions are found in the following list of preferred compound, 4a-hydroxy-4''-epiacetylaminoavermectin $B_1$
4a-hydroxy-4''-epiacetylamino-22,23-dihydroavermectin $B_1$
13-O-methoxyethoxymethyl-4a-hydroxy-22,23-dihydroavermectin $B_1$ aglycone
4a-acetoxy-4''-epiacetylaminoavermectin $B_1$
4a-benzoyloxy-4''-epiacetylaminoavermectin $B_1$
4a-(2-pyrrolecarboxy)-4''-epiacetylaminoavermectin $B_1$
4a-methoxyethoxymethoxy-4''-epiacetylaminoavermectin $B_1$
4''-epiacetylamino-4a-hydroxy-avermectin $B_1$-5-ketoxime
4''-morpholinylcarbonylhydrazonyl-4a-hydroxyavermectin $B_1$
4''-O-(methoxyethoxymethyl)-4a-hydroxyavermectin $B_1$
4'',4a-bis-O-(methoxyethoxymethyl)avermectin $B_1$
4a-benzoyloxy-4''-O-methoxyethoxymethylavermectin $B_1$
4''-O-methoxyethoxymethyl-4a-pyrrolecarboxyavermectin $B_1$
4''-epi-N-acetyl-N-methylamino-4a-hydroxyavermectin $B_1$
4''-epi-acetylamino-4a-(3-pyridinecarboxy) avermectin $B_1$
4''-epi-acetylamino-4a-O-(4-dimethylaminobenzoyl) avermectin $B_1$
4''-O-methoxyethoxymethyl-4a-methylthioavermectin $B_1$
4a-benzyloxymethoxy-4''-O-methoxyethoxymethylavermectin $B_1$
13-O-methoxyethoxymethyl-4a-methoxyethoxymethoxy-22,23-dihydroavermectin $B_1$ aglycone
4''epi-N-acetyl-N-methylamino-4a-methoxyethoxymethoxyavermectin $B_1$
4''-epi-N-acetylamino-4a-benzyloxymethoxyavermectin $B_1$
4''-epi-N-acetylamino-4a-benzyloxyavermectin $B_1$
4''-epi-N-acetylamino-4a-(1-tetrahydropyranyl) oxyavermectin $B_1$
4a-methoxyethoxymethoxy-4''-epiacetylamino-22,23-dihydroavermectin $B_1$
4a-hydroxy-22,23-dihydroavermectin $B_1$ monosaccharide
4a-methoxyethoxymethoxy-4'-O-methoxyethoxymethyl-22,23-dihydroavermectin $B_1$ monosaccharide
4a-methoxyethoxymethoxy-22,23-dihydroavermectin $B_1$ monosaccharide
4''-epi-acetylamino-4a-methylthiomethoxyavermectin $B_1$
4a-methoxyethoxymethoxyavermectin $B_1$
4''-epi-methylsulfonyl-4a-hydroxyavermectin $B_1$
4a-methoxyethoxymethoxy-4''-epi-methylsulfonylavermectin $B_1$
4a-methoxyethoxymethoxy-22,23-dihydroavermectin $B_1$
4a-methoxymethoxyavermectin $B_1$
4''-epi-acetylamino-4a-methoxymethoxy-22,23-dihydroavermectin $B_1$
4''-epi-methoxyacetylamino-4a-methoxyavermectin $B_1$
4''-epi-N-acetyl-N-methylamino-4a-methoxymethoxy-22,23-dihydroavermectin $B_1$
4a-oleandrosyloxyavermectin $B_1$
4a-phenylthio-4''-epiacetyl-aminoavermectin $B_1$ 13-fluoro-4a-methoxyethoxymethoxyavermectin B₁ aglycone 4a-O-methoxyethoxymethoxymoxidectin The compounds of the instant invention are prepared according to the following reaction scheme:

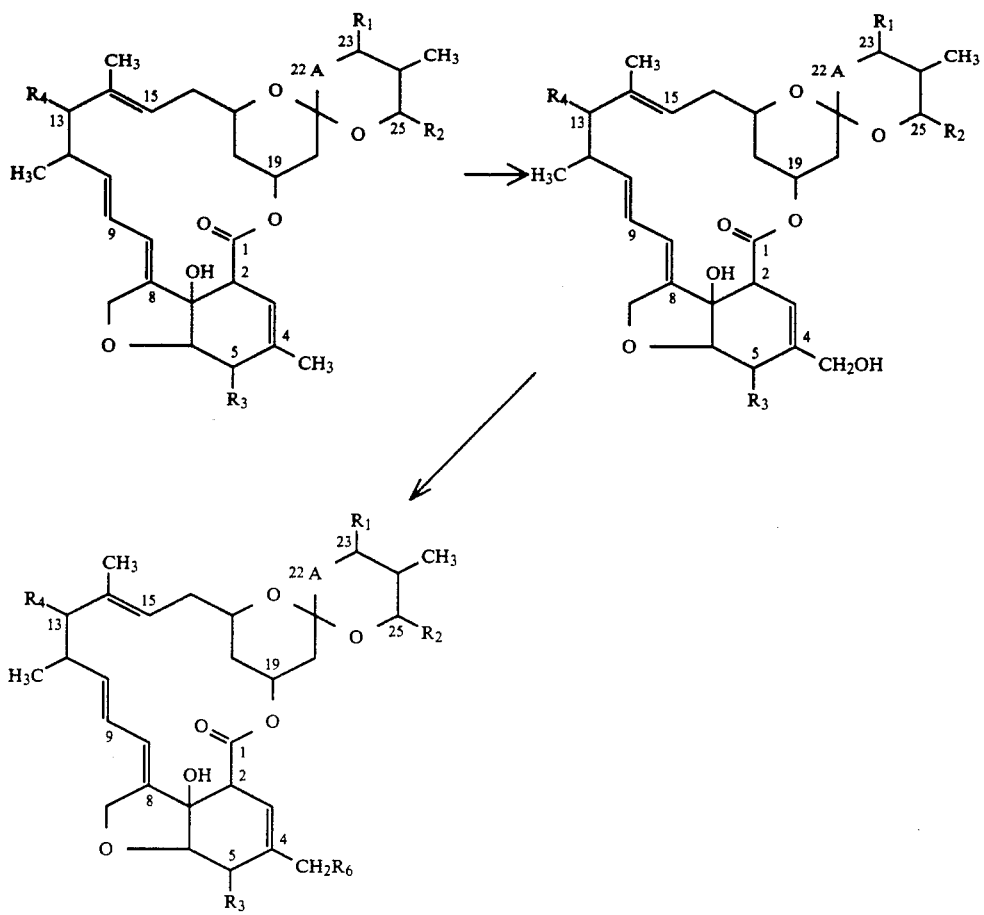

In the foregoing, reaction scheme, $R_1$ $R_2$, $R_3$, $R_4$ and $R_6$ are as defined above.

In the first step of the reaction, the 4-methyl group is oxidized to a 4a-hydroxy methyl group. The rection is carried out preferably with selenium dioxide and an alkyl hydroperoxide, such as t-butyl-hydroperoxide. The reaction is carried out in a solvent inert to oxidation and halogenated hydro-carbons such as methylene chloride are preferred. The reaction may be carried out at from −20° C. to the reflux temperature of the reaction mixture, although room temperature is preferred. The reaction is generally complete in from 4 to 40 hours although the progress of the reaction can be monitored by taking aliquots of the reaction mixture and analyzing for the formation of the oxidized product and disappearance of the starting material. This will determine whether the reaction is completed or not, or if necessary, additional oxidizing reagent can be added to the reaction mixture if it is determined that the reaction has not gone to completion. The products are isolated using techniques known to those skilled in the art.

In the oxidation of the 4a-position care must be taken to avoid reaction at other susceptible positions. In particular hydroxy functions are best protected by preparing the alkanoyl derivatives or the ether protected derivatives such as the silyl derivatives discussed below.

Following the formation of the 4a-hydroxy compound, reactions may be carried out at the 4a-position to prepare the additional 4a-derivative and further reactions may be carried out elsewhere on the molecule. The order of the reactions being carried out is not critical however, one skilled in the art will recognize that certain reactions may occur at more than one position and unwanted by-products may be prepared. At each step in the reaction sequence the use of protecting groups may be necessary or advisable to avoid unwanted reactions.

The acylated derivatives at the 4a-position can be prepared using acylation techniques known to those skilled in the art. One such technique involves the use of triphenylphosphine in an inert solvent such as a halogenated hydrocarbon in the presence of the appropriate carboxylic acid or carboxylic acid derivatives and dialkylazodicarboxylate, preferably diethylazodicarboxylate. The reaction is carried out generally at room temperature although temperature of from −20° C. to the reflux temperature of the reaction mixture are acceptable. The reaction is rapid and generally complete in from 5 to 60 minutes.

The preparation of the poly(alkoxy) dervatives is carried out using the appropriate poly(alkoxy) alkylchloride reagent where the alkyl chloride position of the reagent, in combination with the oxygen of the 4-a-hydroxy group, becomes the innermost alkoxy group of the final product. The reaction is carried out in the presence of a reagent to remove the liberated proton from the possibility of further reaction. Generally an amine is used as the reagent to absorb the liberated proton and trisubstituted amines are preferred. Most appropriate for this purpose is N,N,N',N'-tetramethyl-1,8-diaminonaphthalene. The proton absorbing reagent and the starting material are combined in an inert solvent, polar solvents such as acetonitrile are preferred, and the poly(alkoxy) alkyl chloride is added to the reaction mixture. The reaction is generally carried out at room temperature, preferably about 20° C. although temperatures of from −20° C. to the reflux temperature of the reaction mixture are acceptable. The reaction is generally complete from 1 to 40 hours. The products are isolated using techniques known to those skilled in the art.

During the reactions at the 4a-position it is necessary to protect other hydroxyl groups in the molecule with a protecting group which may be removed after the reaction is accomplished. Typically, hydroxy groups to be protected are found at positions 5, 7, 13, and 23. Suitable protecting groups include tert-butyldimethylsilyl, tert-butyldiphenylsilyl, phenoxyacetyl, acetyl, and the like. The tert-butyldimethylsilyl group is preferred and is introduced by treating a solution of the alcohol in dimethylformamide (DMF) with an excess of imidazole and a silylating reagent such as tert-butyldimethylsilyl-chloride, tert-butyldimethylsilyl-trifluoromethanesulfonate, and the like at temperatures ranging from −20° C. to 50° C. for 1 to 48 hours. The reaction is then worked up and the product is isolated and purified using standard techniques known to those skilled in the art. The protecting group may be removed by treatment with a solution of hydrogen fluoride in a pyridine/tetrahydrofuran solvent mixture. Alternatively, the protecting group may be removed by treatment with a solution of p-toluenesulfonic acid (0.5–2%) in methanol at 0° C. to 25° C. for 0.5 to 8 hours. Deprotection with hydrogen fluoride in pyridine/tetrahydrofuran is preferred. In both cases reaction workup and product isolation and purification are by standard techniques well known to those skilled in the art.

An amino substituent may be introduced at position 4″ by reductive amination of a 4″-ketone which is in turn prepared by oxidation of the 4″-hydroxyl group present in the avermectins. During the oxidation of the hydroxyl group at C-4″ it is necessary to protect other secondary hydroxyl groups in the molecule (note that it is not necessary to protect the tertiary hydroxyl present at position 7) as described above. With other secondary hydroxyl groups protected the hydroxyl group at position 4″ can be oxidized by a variety of methods to afford the ketone derivatives necessary for conversion to amino and acylamino analogs. The oxidation of this hydroxyl group can be effected by using a variety of oxidation procedures, including oxidation with dimethylsulfoxide (DMSO) based systems commonly known to those skilled in the art as Swern (or Moffat) oxidations (DMSO-oxalyl-chloride, DMSO-acetic anhydride, DMSO-trifluoroacetic anhydride and the like) as well as oxidations with chromium based reagents (pyridinium chlorochromate and the like), or other methods known to those skilled in the art. The DMSO based oxidations are preferred. The oxidation reagent is generated by treating a solution of DMSO in a non-nucleophilic solvent such as dichloromethane (preferred), chloroform, ether, tetrahydrofuran and the like with an electrophilic activating agent such as oxalyl chloride (preferred), dicyclohexylcarbodiimide (DCC), phosgene, and the like at temperatures ranging from −90° C. to −55° C. and stirring the mixture thus formed at this temperature for 10 to 90 minutes. To the oxidizing reagent thus generated is added, at the same temperature, a solution of the alcohol in the solvent used to generate the reagent. The solution is stirred at temperatures ranging from −90° C. to −55° C. for 10 to 90 minutes hindered base such as triethylamine, diisopropylethylamine, and the like is added. The temperature is raised to 0° C. to 30° C. and the mixture stirred at this temperature for 10 to 90 minutes. The reaction is then worked up using standard techniques known to those skilled in the art and the crude product thus obtained is typically used without further purification.

The 4″-ketone functionality thus generated may be used to introduce amino substituents at position 4″ via a reductive amination reaction. The reductive amination affords an avermectin mixture consisting of both possible stereoisomers at position 4″ (4″-alpha-amino and 4″-beta-amino) which is referred to herein as 4″-aminoavermectin. The reductive amination is accomplished by treating a solution of the ketone in an alcoholic solvent such as methanol, ethanol, and the like with an ammonium salt such as ammonium acetate (preferred), ammonium formate, ammonium benzoate and the like at temperatures ranging from −25° C. to 25° C. for 15 to 60 minutes then adding sodium cyanoborohydride to the resulting mixture and stirring at temperatures ranging from 0° C. to 30° C. for 30 to 90 minutes. The reaction is then worked up and the product is isolated and purified using standard techniques known to those skilled in the art. The reaction may be modified by substituting an alkylammonium salt in the place of ammonium acetate in the above procedure to prepare avermectin derivatives substituted with an alkylamino group at the 4″ position. Reaction of the 4″-ketone with ammonium acetate or alkylammonium acetate in methanol followed by addition of sodium cyanoborohydride is preferred.

The amino (or alkylamino) substituted derivatives prepared as described above may be acylated to provide acylamino analogs. The acylation is accomplished by treating a solution of the 4″-amino or 4″-alkylamino analog in a halogenated solvent such as dichloromethane, chloroform or the like, or, preferably, esters such as ethyl acetate, with one molar equivalent of an acylating agent such as an alkanoyl chloride (preferred), alkanoyl bromide, alkanoic acid in combination with dicyclohexylcarbodiimide, and the like in the presence of a base such as triethylamine, pyridine and the like with or without the addition of a nucleophilic catalyst such as dimethylaminopyridine at temperatures ranging from −10° C. to 35° C. for 15 minutes to 24 hours. The reaction is then worked up and the product is isolated and purified using standard techniques known to those skilled in the art. Note that it is not necessary to protect secondary alcohols in the molecule during the acylation reaction as the amino functionality is sufficiently more reactive that acylation occurs selectively at nitrogen.

After the reactions at the 4a-position, an oxime may be generated at position 5 via the 5-ketone. This ketone is prepared by oxidation of a compound with a 5-hydroxyl group using one of the oxidation methods described above, however oxidation with manganese dioxide or pyridinum dichromate in dimethyl formamide is preferred. The oxidation is carried out by treating a solution of the alcohol in a non-hydroxylic solvent such as benzene, dichloromethane, chloroform, tetrahydrofuran, and the like with an excess of manganese dioxide at temperatures ranging from 25° C. to the reflux temperature of the solvent for 4 to 48 hours. The reaction is worked up and the product is isolated and purified using standard techniques known to those skilled in the art. The ketone thus generated may be used to prepare oximes or alkoximes by a number of procedures. Generally, an excess of hydroxylamine hydrochloride or the appropriate alkoxylamine hydrochloride (methoxylamine hydrochloride for a methoxime, etc.) is added to a solution of the ketone in pyridine and the solution stirred at temperatures ranging from 0° C. to 50° C. for 3-36 hours. Preferably 0-(trimethylsilyl) hydroxylamine and zinc chloride is used to form the oxime. The reaction is carried out in a polar solvent such as an ester, ethyl acetate being preferred at from −20° C. to the reflux temperature of the reaction mixture. The reaction is generally complete in from 1 to 40 hours. Alternatively the amine hydrochloride is added to a solution of the ketone in a neutral solvent such as benzene, tetrahydrofuran, dioxane, dichloromethane, ethanol, and the like followed by a molar equivalent of a base such as sodium acetate, sodium hydroxide, triethylamine, and the like. The resulting mixture is stirred at temperatures ranging from 0° C. to 50° C. for 3-36 hours. In either case the reaction is worked up and the product is isolated and purified using standard techniques known to those skilled in the art.

The instant compounds of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, horseflies, screwworm flies, warble flies, heelflies, deerflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gasterophilus in horses.

The instant compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongyloides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), *Musca domestica* (housefly), *Solenopsis Invicta* (imported fire ant) little housefly, (*Fannia canicularis*) and the darkling beetle in poultry operations.

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as nematodicides for the control of soil nematodes which are important to the agricultural community.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in animal feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts. The compounds of this invention may also be applied to premeses as a spray, paint or wipe oe they may be added to baits. The techniques for applying these compounds are known to those skilled in environmental pest control.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, elemental analysis, and the like. Being amorphous the compounds are not characterized by sharp melting points but the chromatographic and analytical methods employed indicate that they are pure.

General. Analytical thin layer chromatography (TLC) was performed on EM Reagents 0.25 mm silica gel 60-F plates. Visualization was accomplished with UV light and by dipping in an aqueous ceric ammonium molybdate solution followed by heating. Solvents for extraction were reagent grade. Solvents for reactions were dried with 3-Å or 4-Å molecular sieves. All reactions were performed under an inert atmosphere of dry nitrogen in dry glassware. $^1$H NMR spectra were recorded in deuterochloroform on a Varian XL-300 (299.94 MHz) spectrometer. Chemical shifts are reported in ppm from an internal standard of residual chloroform (7.27 ppm). Selected data are reported as follows: chemical shift, multiplicity (s=singlet, d=doublet, t=triplet, q=quartet, m=multiplet, br=broadened, om=overlapping multiplet), coupling constants (Hz), and assignments. Assignments were made with the aid of 2D (COSY) data. $^{13}$C NMR spectra were recorded in deuterochloroform on a Varian XL-300 (75.4 MHz) spectrometer. Chemical shifts are reported in ppm from the central peak of deuterochloroform (77.0 ppm). Assignments were made with the aid of APT data. Data are reported as follows: chemical shift, assignment. Combustion analyses were obtained from Microlit Laboratories, Inc., Caldwell, N.J., or Robertson Laboratory, Inc., Madison, N.J.

EXAMPLE 1

4a-Hydroxy-4"-epiacetylaminoavermectin $B_1$

A 250-mL round-bottom flask fitted with a magnetic stirring bar, septum and nitrogen inlet was charged with 12.0 g (13.1 mmol) of 4"-epiacetylaminoavermectin $B_1$ in 90 mL of dichloromethane. To the resulting clear solution was added 729 mg (6.57 mmol) of selenium dioxide followed by 5.80 mL (5.22 g, 52.5 mmol) of 90% tert-butylhydroperoxide at room temperature. After 22 h, 1.45 mL (1.30 g, 13 mmol) of 90% tert-butylhydroperoxide was added. The resulting solution was stirred at room temperature for 5 h. The reaction mixture was then concentrated by rotary evaporation and chromatographed (7 cm×30 cm column, 96:4 dichloromethane:methanol for 4 L, then a gradient in 1.5 L, 0.5% methanol increments to 92:8 dichloromethane:methanol) to provide 6.10 g (50%) of 4a-hydroxy-4″-epiacetylaminoavermectin $B_1$ as a foam: $R_f=0.27$ (93:7 dichloromethane/methanol);

$^1$H NMR δ 5.86 (m, $H_9$), 5.78–5.63 (om, $H_3$, $H_{10}$, $H_{11}$, $H_{22}$, NH), 5.55 (dd, J=9.9, 2.5, $H_{23}$), 5.38–5.25 (om, $H_{19}$, $H_{1″}$), 4.95 (m, $H_{15}$), 4.74 (d, J=3.2, $H_{1′}$), 4.65 (m, $H_{8a}$), 4.55 (br d, J=5.0, $H_5$), 4.38, (dd, J=10.0, 3.2, $H_{4″}$), 4.22 (brs, $H_{4a}$), 4.03 (m, $H_{5″}$), 3.97 (d, J=6.3, $H_6$), 3.90 (brs, $H_{13}$), 3.90–3.72 (om, $H_{17}$, $H_{5′}$), 3.71–3.50 (om, $H_{3′}$, $H_{3″}$), 3.45 (d, J=10, $H_{25}$), 3.42 (s, $OCH_3$), 3.35 (s, $OCH_3$), 3.32 (m, $H_2$), 3.18 (t, J=9.0, $H_{4′}$), 2.70 (brs, 2×OH), 2.50 (m, $H_{12}$), 2.32–2.15 (om, 2×$H_{16}$, $H_{24}$, $H_{2′eq}$), 2.07 (s, $CH_3CO$), 2.05–1.95 (om, $H_{20eq}$, $H_{2″eq}$), 1.75 (m, $H_{18eq}$), 1.65–1.40 (om, $H_{20}$, $H_{26}$, 2×$H_{27}$, $H_{2′}$, $H_{2″}$), 1.48 (s, 3×$H_{14a}$), 1.21 (d, J=6.2, 3×$H_{6′}$), 1.15 (d, J=6.9, 3×$H_{12a}$), 1.10 (d, J=6.6, 3×$H_{6″}$), 0.95–0.85 (om, 3×$H_{24a}$, 3×$H_{26a}$, 3×$H_{28}$, $H_{18ax}$); $^{13}$C NMR δ 173.2 ($C_1$), 170.9 ((C=O)NH), 140.2, 139.3 ($C_4$, $C_8$), 138.1 ($C_{11}$), 136.3 ($C_{22}$), 135.1 ($C_{14}$), 127.7 ($C_{23}$), 124.7 ($C_{10}$), 120.7, 119.9, 118.3 ($C_3$, $C_9$, $C_{15}$), 98.6 ($C_{1″}$), 95.8 ($C_{21}$), 94.9 ($C_{1′}$), 81.9 ($C_{13}$), 81.0 ($C_{4′}$), 80.6 ($C_7$), 79.3 ($C_{3′}$), 79.2 ($C_6$), 74.9 ($C_{25}$), 73.3 ($C_{3″}$), 68.6, 68.3 ($C_{17}$, $C_{19}$), 68.4 ($C_{8a}$), 67.1, 65.5 ($C_5$, $C_{5′}$, $C_{5″}$), 64.4 ($C_{4a}$), 56.6, 56.1 (2×$OCH_3$), 48.5 ($C_{4″}$), 45.6 ($C_2$), 40.5 ($C_{20}$), 39.8 ($C_{12}$), 36.5 ($C_{18}$), 35.2 ($C_{26}$), 34.5 ($C_{2′}$), 34.2 ($C_{16}$), 31.8 ($C_{2″}$), 30.6 ($C_{24}$), 27.5 ($C_{27}$), 23.4 ($CH_3C=O$), 20.2 ($C_{12a}$), 18.3 ($C_{6′}$), 17.0 ($C_{6″}$), 16.4 ($C_{24a}$), 15.1 ($C_{14a}$), 13.0 ($C_{26a}$), 12.0 ($C_{28}$); MS (FAB) 952 (M+Na, 4), 330 (26), 305 (22), 300 (20), 221 (20), 186 (100), 154 (82), 112 (34). Anal. Calcd for $C_{50}H_{75}NO_{15}$: C, 64.57; H, 7.95; N, 1.51. Found: C, 64.53; H, 7.95; N, 1.52.

EXAMPLE 2

4a-Hydroxy-4″-epiacetylamino-22,23-dihydroavermectin $B_1$

Using the same procedure as Example 1, 4a-hydroxy-4″-epiacetylamino-22,23-dihydroavermectin $B_1$ was prepared from 4″-epiacetylamino-22,23-dihydroavermectin $B_1$: yield 404 mg (40%), isolated as a foam: $R_f=0.27$ (96:4 dichloromethane/methanol);

$^1$H NMR δ 5.86 (m, $H_9$), 5.78–5.63 (om, $H_3$, $H_{10}$, $H_{11}$, NH), 5.38–5.25 (om, $H_{19}$, $H_{1″}$), 4.95 (m, $H_{15}$), 4.74 (d, J=3.2, $H_{1′}$), 4.65 (m, $H_{8a}$), 4.55 (br d, J=5.0, $H_5$), 4.40, (dd, J=10.0, 3.2, $H_{4″}$), 4.25 (m, $H_{4a}$), 4.03 (m, $H_{5″}$), 3.92 (d, J=6.3, $H_6$), 3.90 (brs, $H_{13}$), 3.88–3.72 (m, $H_{17}$), 3.71–3.50 (om, $H_{3′}$, $H_{3″}$, $H_{5′}$), 3.42 (s, $OCH_3$), 3.35 (s, $OCH_3$), 3.32 (m, $H_2$), 3.18 (t, J=9.0, $H_{4′}$), 2.70 (brs, 2×OH), 2.50 (m, $H_{12}$), 2.32–2.15 (om, 2×$H_{16}$, $H_{24}$, $H_{2′eq}$), 2.07 (s, $CH_3CO$), 2.05–1.95 (om, $H_{20eq}$, $H_{2″eq}$), 1.75 (m, $H_{18eq}$), 1.65–1.40 (om, $H_{20}$, 2×$H_{22}$, $H_{26}$, 2×$H_{27}$, $H_{2′}$, $H_{2″}$), 1.48 (s, 3×$H_{14a}$), 1.21 (d, J=6.2, 3×$H_{6′}$), 1.15 (d, J=6.9, 3×$H_{12a}$), 1.10 (d, J=6.6, 3×$H_{6″}$), 0.95–0.85 (om, 3×$H_{24a}$, 3×$H_{26a}$, 3×$H_{28}$, $H_{18ax}$);

$^{13}$C NMR δ 173.3 ($C_1$), 170.9 ((C=O)NH), 140.1, 139.3 ($C_4$, $C_8$), 138.1 ($C_{11}$), 135.0 ($C_{14}$), 124.7 ($C_{10}$), 120.7, 119.9, 118.3 ($C_3$, $C_9$, $C_{15}$), 98.6 ($C_{1″}$), 97.5 ($C_{21}$), 94.8 ($C_{1′}$), 81.8 ($C_{13}$), 81.0 ($C_{4′}$), 80.6 ($C_7$), 79.3 ($C_{3′}$), 79.1 ($C_6$), 76.6 ($C_{25}$), 73.3 ($C_{3″}$), 68.9, 67.2 ($C_{17}$, $C_{19}$), 68.5 ($C_{8a}$), 67.0, 65.7, 65.5 ($C_5$, $C_{5′}$, $C_{5″}$), 64.5 ($C_{4a}$), 56.6, 56.1 (2×$OCH_3$), 48.5 ($C_{4″}$), 45.6 ($C_2$), 41.2 ($C_{20}$), 39.7 ($C_{12}$), 36.9 ($C_{18}$), 35.7 ($C_{22}$), 35.4 ($C_{26}$), 34.5 ($C_{2′}$), 34.1 ($C_{16}$), 31.8 ($C_{2″}$), 31.2 ($C_{24}$), 28.1 ($C_{27}$), 27.3 ($C_{23}$), 23.5 ($CH_3C=O$), 20.2 ($C_{12a}$), 18.3 ($C_{6′}$), 17.5 ($C_{6″}$), 17.1 ($C_{24a}$), 15.1 ($C_{14a}$), 12.5 ($C_{26a}$), 12.1 ($C_{28}$); MS (FAB) 938 (M+Li, 100). Anal. Calcd for $C_{50}H_{77}NO_{15}$: C, 64.43; H, 8.33; N, 1.50. Found: C, 64.87; H, 8.43; N, 1.43.

EXAMPLE 3

13-O-Methoxyethoxymethyl-4a-hydroxy-22,23-dihydroavermectin $B_1$ aglycone

Using the same procedure as Example 1, 13-O-methoxyethoxymethyl-4a-hydroxy-22,23-dihydroavermectin $B_1$ aglycone was prepared from 13-O-methoxyethoxymethyl-22,23-dihydroavermectin $B_1$ aglycone: yield 1.36 g (44%), isolated as a foam: $R_f=0.25$ (96:4 dichloromethane/methanol);

$^1$H NMR δ5.82 (m, $H_9$), 5.78–5.63 (om, $H_3$, $H_{10}$, $H_{11}$), 5.30 (m, $H_{19}$), 5.15 (m, $H_{15}$), 4.65 (om, $H_{8a}$, $OCH_2O$), 4.55 (br d, J=5.0, $H_5$), 4.40, (dd, J=10.0, 3.2, $H_{4″}$), 4.25 (m, $H_{4a}$), 4.15 (s, 7-OH), 3.98–3.85 (om, $H_6$, $H_{13}$, $H_{15}$), 3.70–3.55 (m, $H_{17}$, $OCH_2CH_2OCH_3$), 3.55 (m, $OCH_2CH_2OCH_3$), 3.37 (s, $OCH_3$), 3.29 (m, $H_2$), 3.18 (m, $H_{25}$), 2.70 (brs, OH), 2.50 (m, $H_{12}$), 2.32–2.15 (m, 2×$H_{16}$), 1.96 (m, $H_{20eq}$), 1.75 (m, $H_{18eq}$), 1.65–1.30 (om, $H_{20}$, 2×$H_{22}$, 2×$H_{23}$, $H_{26}$, 2×$H_{27}$), 1.48 (s, 3×$H_{14a}$), 1.12 (d, J=6.7, 3×$H_{12a}$), 0.93 (d, J=7.1, 3×$H_{28}$), 0.85–0.75 (om, 3×$H_{24a}$, 3×$H_{26a}$, $H_{18ax}$);

$^{13}$C NMR d 173.2 ($C_1$), 139.9, 139.3 ($C_4$, $C_8$), 138.3 ($C_{11}$), 135.1 ($C_{14}$), 124.6 ($C_{10}$), 120.7, 120.0, 118.2 ($C_3$, $C_9$, $C_{15}$), 97.4 ($C_{21}$), 94.4 ($OCH_2O$), 82.5 ($C_{13}$), 80.4 ($C_7$), 78.9 ($C_6$), 77.4 ($C_{25}$), 71.8, 67.2 ($OCH_2CH_2O$), 68.8, 67.6 ($C_{17}$, $C_{19}$), 68.6 ($C_{8a}$), 66.0, ($C_5$), 64.9 ($C_{4a}$), 59.1 ($OCH_3$), 45.5 ($C_2$), 41.2 ($C_{20}$), 39.8 ($C_{12}$), 36.9 ($C_{18}$), 35.8 ($C_{22}$), 35.5 ($C_{26}$), 34.2 ($C_{16}$), 31.2 ($C_{24}$), 28.0 ($C_{27}$), 27.5 ($C_{23}$), 19.6 ($C_{12a}$), 17.5 ($C_{24a}$), 14.9 ($C_{14a}$), 12.6 ($C_{26a}$), 11.7 ($C_{28}$); MS (FAB) 713 (M+Na, 100). Anal. Calcd for $C_{38}H_{58}NO_{11}$: C, 66.06; H, 8.46. Found: C, 65.82; H, 8.56.

EXAMPLE 4

4a-Acetoxy-4″-epiacetylaminoavermectin $B_1$

A 25-mL round-bottom flask fitted with a magnetic stirring bar, septum and nitrogen inlet was charged with 257 mg (276 μmol) of 4a-hydroxy-4″-epiacetylaminoavermectin $B_1$, 94 mg (359 μmol) of $Ph_3P$ and 21 μl (22 mg, 359 μmol) of acetic acid in 5 mL of dichloromethane. To the resulting clear solution was added 56 μl (62 mg, 359 μmol) of diethyl azodicarboxylate at room temperature over 5 min. The resulting solution was stirred at room temperature for 15 min. The reaction was quenched by the addition of 15 mL of saturated aqueous sodium bicarbonate and poured into a separatory funnel containing 15 mL of dichloromethane. The layers were separated and the aqueous layer was extracted with 2×15 mL of dichloromethane. The organic layers were combined, dried over sodium sulfate, filtered concentrated and chromatographed (2 cm×25 cm column, ethyl acetate) to provide 188 mg (70%) of 4a-acetoxy-4″-epiacetylaminoavermectin $B_1$ as a foam: $R_f=0.25$ (ethyl acetate);

$^1$H NMR δ5.86 (m, $H_9$), 5.78–5.68 (om, $H_3$, $H_{10}$, $H_{11}$, NH), 5.58 (d, J=9.9, $H_{22}$), 5.55 (dd, J=9.9, 2.5, $H_{23}$), 5.38–5.25 (om, $H_{19}$, $H_{1″}$), 4.95 (m, $H_{15}$), 4.80–4.60 (om, $H_{1′}$, 2×$H_{8a}$, 2×$H_{4a}$), 4.45 (d, J=5.0, $H_5$), 4.42, (dd, J=10.0, 3.2, $H_{4″}$), 4.03 (m, $H_{5″}$), 3.97 (d, J=6.3, $H_6$), 3.90 (brs, $H_{13}$), 3.90–3.72 (om, $H_{17}$, $H_{5′}$), 3.71–3.52 (om, $H_{3′}$, $H_{3″}$), 3.45 (d, J=10, $H_{25}$), 3.42 (s, $OCH_3$), 3.35 (s, $OCH_3$), 3.32 (m, $H_2$), 3.18 (t, J=9.0, $H_{4′}$), 2.50 (m, $H_{12}$), 2.32–2.15 (om, 2×$H_{16}$, $H_{24}$, $H_{2′eq}$), 2.07 (s, $CH_3CO$), 2.05 (s, CH$_3$CO), 1.95–1.85 (om, H$_{20eq}$, H$_{2''eq}$), 1.75 (m, H$_{18eq}$), 1.65–1.40 (om, H$_{20}$, H$_{26}$, 2×H$_{27}$, H$_{2'}$, H$_{2''}$), 1.48 (s, 3×H$_{14a}$), 1.21 (d, J=6.2, 3×H$_{6'}$), 1.15 (d, J=6.9, 3×H$_{12a}$), 1.10 (d, J=6.6, 3×H$_{6''}$), 0.95–0.85 (om, 3×H$_{24a}$, 3×H$_{26a}$, 3×H$_{28}$, H$_{18ax}$);

$^{13}$C NMR δ173.2 (C$_1$), 170.9, 170.8 (CH$_3$CONH, CH$_3$CO$_2$), 139.3, 136.5 (C$_4$, C$_8$), 138.3 (C$_{11}$), 136.3 (C$_{22}$), 135.1 (C$_{14}$), 127.7 (C$_{23}$), 124.7 (C$_{10}$), 121.6, 120.7, 118.3 (C$_3$, C$_9$, C$_{15}$), 98.6 (C$_{1''}$), 95.8 (C$_{21}$), 94.9 (C$_{1'}$), 81.9 (C$_{13}$), 81.0 (C$_{4'}$), 80.5 (C$_7$), 79.3 (C$_{3'}$), 79.0 (C$_6$), 74.9 (C$_{25}$), 73.3 (C$_{3''}$), 68.7, 68.3 (C$_{17}$, C$_{19}$), 68.5 (C$_{8a}$), 67.1, 65.5, 64.7 (C$_5$, C$_{5'}$, C$_{5''}$), 64.4 (C$_{4a}$), 56.6, 56.1 (2×OCH$_3$), 48.4 (C$_{4''}$), 45.6 (C$_2$), 40.5 (C$_{20}$), 39.8 (C$_{12}$), 36.6 (C$_{18}$), 35.1 (C$_{26}$), 34.5 (C$_{2'}$), 34.2 (C$_{16}$), 31.9 (C$_{2''}$), 30.6 (C$_{24}$), 27.5 (C$_{27}$), 23.5 (CH$_3$CONH), 21.0 (CH$_3$CO$_2$), 20.2 (C$_{12a}$), 18.3 (C$_{6'}$), 17.1 (C$_{6''}$), 16.4 (C$_{24a}$), 15.1 (C$_{14a}$), 13.0 (C$_{26a}$), 12.0 (C$_{28}$); MS (FAB) 972 (M+H, 100). Anal. Calcd for C$_{52}$H$_{77}$NO$_{16}$: C, 64.24; H, 7.98; N, 1.44. Found: C, 64.58; H, 7.86; N, 1.08.

EXAMPLE 5

4a-Benzoyloxy-4''-epiacetylaminoavermectin B$_1$

A 25-mL round-bottom flask fitted with a magnetic stirring bar, septum and nitrogen inlet was charged with 402 mg (432 μmol) of 4a-hydroxy-4''-epiacetylaminoavermectin B$_1$, 142 mg (540 μmol) of Ph$_3$P and 132 mg (1.08 mmol) of benzoic acid in 4 mL of dichloromethane. To the resulting clear solution was added 85 μl (94 mg, 540 μmol) of diethyl azodicarboxylate at room temperature over 5 min. The resulting solution was stirred at room temperature for 15 min. The reaction was quenched by the addition of 15 mL of saturated aqueous sodium bicarbonate and poured into a separatory funnel containing 15 mL of dichloromethane. The layers were separated and the aqueous layer was extracted with 2×15 mL of dichloromethane. The organic layers were combined, dried over sodium sulfate, filtered concentrated and chromatographed (2 cm×25 cm column, 97:3 dichloromethane:methanol) to provide 374 mg (84%) of 4a-benzoyl-4''-epiacetylaminoavermectin B$_1$ as a foam: R$_f$=0.25 (97:3 dichloromethane:methanol);

$^1$H NMR δ8.05 (m, 2×arom. H), 7.55 (m, arom. H), 7.40 (m, 2×arom. H), 5.86 (m, H$_9$), 5.81 (m, H$_3$), 5.78–5.68 (om, H$_{10}$, H$_{11}$, NH), 5.58 (d, J=9.9, H$_{22}$), 5.52 (dd, J=9.9, 2.5, H$_{23}$), 5.45–5.30 (om, H$_{19}$, H$_{1''}$), 5.05–4.88 (m, 2×H$_{4a}$, H$_{15}$), 4.74 (d, J=3.1, H$_{1'}$), 4.68 (m, 2×H$_{8a}$), 4.54 (d, J=5.0, H$_5$), 4.40, (dd, J=10.0, 3.2, H$_{4''}$), 4.03 (m, H$_{5''}$), 4.00 (d, J=6.3, H$_6$), 3.90 (brs, H$_{13}$), 3.90–3.68 (om, H$_{17}$, H$_{5'}$), 3.71–3.52 (om, H$_{3'}$, H$_{3''}$), 3.45 (d, J=10, H$_{25}$), 3.41 (s, OCH$_3$), 3.37 (om, OCH$_3$, H$_2$), 3.18 (t, J=9.0, H$_{4'}$), 2.75 (m, OH), 2.50 (m, H$_{12}$), 2.32–2.15 (om, 2×H$_{16}$, H$_{24}$, H$_{2'eq}$), 2.04 (s, CH$_3$CO), 1.95–1.85 (om, H$_{20eq}$, H$_{2''eq}$), 1.75 (m, H$_{18eq}$), 1.65–1.40 (om, H$_{20}$, H$_{26}$, 2×H$_{27}$, H$_{2'}$, H$_{2''}$), 1.47 (s, 3×H$_{14a}$), 1.21 (d, J=6.2, 3×H$_{6'}$), 1.15 (d, J=6.9, 3×H$_{12a}$), 1.10 (d, J=6.6, 3×H$_{6''}$), 0.95–0.85 (om, 3×H$_{24a}$, 3×H$_{28}$, H$_{18ax}$);

$^{13}$C NMR δ173.2 (C$_1$), 170.7 (CH$_3$CONH), 166.3 (ArCO$_2$), 139.3 (C$_8$), 138.2 (C$_{11}$), 136.7 (C$_4$), 136.3 (C$_{22}$), 135.1 (C$_{14}$), 133.1 (arom), 129.9 (3×arom), 128.4 (2×arom), 127.7 (C$_{23}$), 124.7 (C$_{10}$), 121.5, 120.7, 118.3 (C$_3$, C$_9$, C$_{15}$), 98.7 (C$_{1''}$), 95.8 (C$_{21}$), 94.9 (C$_{1'}$), 81.9 (C$_{13}$), 81.0 (C$_{4'}$), 80.5 (C$_7$), 79.3 (C$_{3'}$), 79.0 (C$_6$), 74.9 (C$_{25}$), 73.3 (C$_{3''}$), 68.6, 68.3 (C$_{17}$, C$_{19}$), 68.5 (C$_{8a}$), 67.1, 65.5, 64.4 (C$_5$, C$_{5'}$, C$_{5''}$), 64.8 (C$_{4a}$), 56.6, 56.1 (2×OCH$_3$), 48.4 (C$_{4''}$), 45.6 (C$_2$), 40.4 (C$_{20}$), 39.8 (C$_{12}$), 36.6 (C$_{18}$), 35.1 (C$_{26}$), 34.5 (C$_{2'}$), 34.3 (C$_{16}$), 31.9 (C$_{2''}$), 30.6 (C$_{24}$), 27.5 (C$_{27}$), 23.5 (CH$_3$CONH), 20.2 (C$_{12a}$), 18.3 (C$_{6'}$), 17.1 (C$_{6''}$), 16.4 (C$_{24a}$), 15.1 (C$_{14a}$), 13.0 (C$_{26a}$), 12.0 (C$_{28}$); MS (FAB) 1040 (M+Li, 100). Anal. Calcd for C$_{57}$H$_{79}$NO$_{16}$: C, 66.20; H, 7.70; N, 1.35. Found: C, 66.40; H, 7.68; N, 1.42.

EXAMPLE 6

4a-(2-Pyrrolecarbonyloxy)-4''-epiacetylaminoavermectin B$_1$

A 25-mL round-bottom flask fitted with a magnetic stirring bar, septum and nitrogen inlet was charged with 380 mg (409 μmol) of 4a-hydroxy-4''-epiacetylaminoavermectin B$_1$, 145 mg (551 μmol) of Ph$_3$P and 123 mg (1.10 mmol) of pyrrole-2-carboxylic acid in 3 mL of dichloromethane. To the resulting clear solution was added 86 μl (95 mg, 550 μmol) of diethyl azodicarboxylate at room temperature over 5 min. The resulting solution was stirred at room temperature for 15 min. The reaction was quenched by the addition of 15 mL of saturated aqueous sodium bicarbonate and poured into a separatory funnel containing 15 mL of dichloromethane. The layers were separated and the aqueous layer was extracted with 2×15 mL of dichloromethane. The organic layers were combined, dried over sodium sulfate, filtered concentrated and chromatographed (3 cm×25 cm column, 96.5:3.5 dichloromethane:methanol) to provide 368 mg (88%) of 4a-(2-pyrrolecarbonyloxy)-4''-epiacetylaminoavermectin B$_1$ as a foam: R$_f$=0.25 (96.5:3.5 dichloromethane:methanol);

$^1$H NMR δ9.62 (brs, arom NH), 6.93 (t, J=2.9, arom H$_3$, H$_5$), 6.22 (q, J=2.9, arom H$_4$), 5.86 (m, H$_9$), 5.80–5.68 (om, H$_3$, H$_{10}$, H$_{11}$, H$_{22}$, NH), 5.51 (d, J=9.9, 2.5, H$_{23}$), 5.40–5.28 (om, H$_{19}$, H$_{1''}$), 5.00–4.80 (m, 2×H$_{4a}$, H$_{15}$), 4.74 (d, J=3.1, H$_{1'}$), 4.68 (m, 2×H$_{8a}$), 4.50 (m, H$_5$), 4.40, (dd, J=10.0, 3.2, H$_{4''}$), 4.20 (s, 7-OH), 4.05 (m, H$_{5''}$), 3.98 (d, J=6.3, H$_6$), 3.90 (brs, H$_{13}$), 3.90–3.68 (om, H$_{17}$, H$_{5'}$), 3.71–3.52 (om, H$_{3'}$, H$_{3''}$), 3.45 (d, J=10, H$_{25}$), 3.41 (s, OCH$_3$), 3.37 (om, OCH$_3$), 3.32 (m, H$_2$), 3.18 (t, J=9.0, H$_{4'}$), 3.00 (m, OH), 2.50 (m, H$_{12}$), 2.32–2.12 (om, 2×H$_{16}$, H$_{24}$, H$_{2'eq}$), 2.03 (s, CH$_3$CO), 2.08–1.95 (om, H$_{20eq}$, H$_{2''eq}$), 1.75 (m, H$_{18eq}$), 1.68–1.40 (om, H$_{20}$, H$_{26}$, 2×H$_{27}$, H$_{2'}$, H$_{2''}$), 1.46 (s, 3×H$_{14a}$), 1.20 (d, J=6.2, 3×H$_{6'}$), 1.15 (d, J=6.9, 3×H$_{12a}$), 1.10 (d, J=6.6, 3×H$_{6''}$), 0.95–0.85 (om, 3×H$_{24a}$, 3×H$_{26a}$, 3×H$_{28}$, H$_{18ax}$);

$^{13}$C NMR δ173.0 (C$_1$), 170.9 (CH$_3$CONH), 160.9 (ArCO$_2$), 139.2 (C$_8$), 138.2 (C$_{11}$), 136.6 (C$_4$), 136.3 (C$_{22}$), 135.1 (C$_{14}$), 128.3 (arom C$_2$), 127.7 (C$_{23}$), 124.7 (C$_{10}$), 123.4 (arom C$_5$), 121.1, 120.7, 118.3 (C$_3$, C$_9$, C$_{15}$), 116.0 (arom C$_3$), 110.5 (arom C$_4$), 98.7 (C$_{1''}$), 95.8 (C$_{21}$), 94.9 (C$_{1'}$), 81.9 (C$_{13}$), 81.0 (C$_{4'}$), 80.5 (C$_7$), 79.3 (C$_{3'}$), 79.1 (C$_6$), 74.9 (C$_{25}$), 73.3 (C$_{3''}$), 68.7, 68.3 (C$_{17}$, C$_{19}$), 68.4 (C$_{8a}$), 67.1, 65.5, 64.7 (C$_5$, C$_{5'}$, C$_{5''}$), 64.1 (C$_{4a}$), 56.6, 56.1 (2×OCH$_3$), 48.4 (C$_{4''}$), 45.6 (C$_2$), 40.5 (C$_{20}$), 39.8 (C$_{12}$), 36.5 (C$_{18}$), 35.1 (C$_{26}$), 34.5 (C$_{2'}$), 34.2 (C$_{16}$), 31.8 (C$_{2''}$), 30.6 (C$_{24}$), 27.5 (C$_{27}$), 23.5 (CH$_3$CONH), 20.2 (C$_{12a}$), 18.3 (C$_{6'}$), 17.1 (C$_{6''}$), 16.4 (C$_{24a}$), 15.1 (C$_{14a}$), 13.0 (C$_{26a}$), 12.1 (C$_{28}$); MS (FAB) 1029 (M+Li, 100). Anal. Calcd for C$_{55}$H$_{78}$N$_2$O$_{16}$: C, 64.56; H, 7.68; N, 2.74. Found: C, 64.91; H, 7.65; N, 2.70.

EXAMPLE 7

4a-Methoxyethoxymethoxy-4''-epiacetylaminoavermectin B$_1$ (A) 4a-tert-Butyldimethylsilyloxy-4''-epiacetylaminoavermectin B$_1$. A 100-mL round-bottom flask fitted with a magnetic stirring bar, septum and nitrogen inlet was charged with 4.58 g (4.93 mmol) of 4a-hydroxy-4"-epiacetylaminoavermectin $B_1$ (see Example 1) in 27 mL of dichloromethane. To the clear solution was added 180 mg (1.48 mmol) of N,N-dimethylaminopyridine and 1.10 mL (799 mg, 7.88 mmol) of triethylamine followed by 965 mg (6.40 mmol) of t-butylchlorodimethylsilane. After stirring at 20° C. for 17 h, 390 mg (2.58 mmol) of t-butylchlorodimethylsilane and 345 μl (250 mg, 2.48 mmol) of triethylamine were added. After stirring for another 5 h, the reaction mixture was added to 50 mL of water. The layers were separated and the aqueous phase was extracted with 5×40 mL of dichloromethane. The organic layers were combined, washed with 200 mL of saturated aqueous sodium bicarbonate, 2×100 mL of water, and 150 mL of saturated aqueous sodium chloride. The organic phase was then dried over sodium sulfate, filtered, concentrated and chromatographed (7 cm×30 cm column, 96.5:3.5 dichloromethane:methanol) to afford 4.20 g (82%) of the silyl ether as a foam: $R_f$=0.16 (96.5:3.5 dichloromethane:methanol);

$^1$H NMR δ5.86 (m, $H_9$), 5.78–5.65 (om, $H_3$, $H_{10}$, $H_{11}$, $H_{22}$), 5.55 (om, $H_{23}$, NH), 5.45–5.30 (om, $H_{19}$, $H_{1''}$), 4.95 (m, $H_{15}$), 4.74 (d, J=3.1, $H_{1'}$), 4.68 (m, 2×$H_{8a}$), 4.50–4.30 (om, $H_5$, 2×$H_{4a}$, $H_{4''}$), 4.10–4.00 (m, $H_{5''}$, 7-OH), 3.98 (d, J=6.3, $H_6$), 3.90 (brs, $H_{13}$), 3.90–3.68 (om, $H_{17}$, $H_{5'}$), 3.71–3.52 (om, $H_{3'}$, $H_{3''}$), 3.45 (d, J=10, $H_{25}$), 3.41 (s, OCH$_3$), 3.37 (s, OCH$_3$), 3.32 (m, $H_2$), 3.18 (t, J=9.0, $H_{4'}$), 2.75 (m, 5-OH), 2.50 (m, $H_{12}$), 2.32–2.12 (om, 2×$H_{16}$, $H_{24}$, $H_{2'eq}$), 2.03 (s, CH$_3$CO), 2.08–1.95 (om, $H_{20eq}$, $H_{2''eq}$), 1.75 (m, $H_{18eq}$), 1.68–1.40 (om, $H_{20}$, $H_{26}$, 2×$H_{27}$, $H_{2'}$, $H_{2''}$), 1.46 (s, 3×$H_{14a}$), 1.22 (d, J=6.2, 3×$H_{6'}$), 1.15 (d, J=6.9, 3×$H_{12a}$), 1.10 (d, J=6.6, 3×$H_{6''}$), 0.95–0.85 (om, 3×$H_{24a}$, 3×$H_{26a}$, 3×$H_{28}$, $H_{18ax}$, SiC(CH$_3$)$_3$), 0.05 (s, Si(CH$_3$)$_2$); MS (FAB) 1066 (M+Na, 100). Anal. Calcd for $C_{56}H_{89}NO_{15}Si$: C, 64.40; H, 8.59; N, 1.34. Found: C, 64.67; H, 8.60; N, 1.22.

(B) 4a-tert-Butyldimethylsilyloxy-5-O-phenoxyacetyl-4"-epiacetylaminoavermectin $B_1$. A 250-mL round-bottom flask fitted with a magnetic stirring bar, septum and nitrogen inlet was charged with 4.20 g (4.02 mmol) of 4a-tert-butyldimethyl silyloxy-4"-epiacetylaminoavermectin $B_1$ in 40 mL of dichloromethane. To the clear solution was added 492 mg (4.02 mmol) of N,N-dimethylaminopyridine and 3.3 mL (3.2 g, 41 mmol) of pyridine followed by 700 μl (865 mg, 5.07 mmol) of phenoxyacetyl chloride. After stirring at 20° C. for 40 min, 50 mL of 1.0M aqueous sodium hydrogen sulfate was added. The resulting mixture was stirred for 10 min, then transferred to a separatory funnel. The layers were separated and the aqueous phase was extracted with 4×40 mL of dichloromethane. The organic layers were combined, washed with 2×50 mL of saturated aqueous sodium bicarbonate and 50 mL of saturated aqueous sodium chloride. The organic phase was then dried over sodium sulfate, filtered, concentrated and chromatographed (5 cm×23 cm column, 97:3 dichloromethane:methanol) to afford 4.60 g (97%) of the silyl ether-ester as a foam: $R_f$=0.23 (97:3 dichloromethane:methanol);

$^1$H NMR δ7.30 (m, arom 2×H), 7.15–6.90 (om, arom 3×H), 5.86 (om, $H_3$, $H_9$), 5.82–5.70 (om, $H_5$, $H_{10}$, $H_{11}$, $H_{22}$), 5.60 (om, $H_{23}$, NH), 5.50–5.38 (om, $H_{19}$, $H_{1''}$), 5.00 (m, $H_{15}$), 4.80 (d, J=3.1, $H_{1'}$), 4.70 (s, OCH$_2$Ar), 4.65 (m, 2×$H_{8a}$), 4.45 (dd J=10.0, 3.2, $H_{4''}$), 4.15 (d, J=6.3, $H_6$), 4.10 (brs, $H_{4a}$), 4.05 (m, $H_{5''}$), 3.97 (s, 7-OH), 3.90–3.70 (om, $H_{17}$, $H_{5'}$), 3.68–3.45 (om, $H_{3'}$, $H_{3''}$), 3.45 (d, J=10, $H_{25}$), 3.41 (s, OCH$_3$), 3.37 (om, OCH$_3$, $H_2$), 3.18 (t, J=9.0, $H_{4'}$), 2.50 (m, $H_{12}$), 2.32–2.12 (om, 2×$H_{16}$, $H_{24}$, $H_{2'eq}$), 2.04 (s, CH$_3$CO), 2.08–1.95 (om, $H_{20eq}$, $H_{2''eq}$), 1.75 (m, $H_{18eq}$), 1.68–1.40 (om, $H_{20}$, $H_{26}$, 2×$H_{27}$, $H_{2'}$, $H_{2''}$), 1.48 (s, 3×$H_{14a}$), 1.21 (d, J=6.2, 3×$H_{6'}$), 1.13 (d, J=6.9, 3×$H_{12a}$), 1.11 (d, J=6.6, 3×$H_{6''}$), 0.95–0.85 (om, 3×$H_{24a}$, 3×$H_{26a}$, 3×$H_{28}$, $H_{18ax}$, SiC(CH$_3$)$_3$), 0.05 (s, Si(CH$_3$)$_2$);

$^{13}$C NMR δ173.0 ($C_1$), 170.7 (CH$_3$CONH), 169.8 (ArCO$_2$), 147.2 (aromC), 139.2 ($C_8$), 138.1 ($C_{11}$), 136.4 ($C_4$), 136.3 ($C_{22}$), 135.1 ($C_{14}$), 129.5 (2×aromC), 127.8 ($C_{23}$), 124.8 ($C_{10}$), 121.7 (aromC), 121.2, 120.8, 118.3 ($C_3$, $C_9$, $C_{15}$), 114.6 (2×aromC), 98.7 ($C_{1''}$), 95.8 ($C_{21}$), 94.9 ($C_{1'}$), 81.9 ($C_{13}$), 81.0 ($C_{4'}$), 80.9 ($C_7$), 79.3 ($C_{3'}$), 77.2 ($C_6$), 74.9 ($C_{25}$), 73.3 ($C_{3''}$), 68.5, 68.3 ($C_{17}$, $C_{19}$), 68.4 ($C_{8a}$), 67.9, 67.1, 65.5 ($C_5$, $C_{5'}$, $C_{5''}$), 64.0 ($C_{4a}$), 63.1 (OCH$_2$Ar), 56.7, 56.1 (2×OCH$_3$), 48.4 ($C_{4''}$), 45.5 ($C_2$), 40.4 ($C_{20}$), 39.8 ($C_{12}$), 36.6 ($C_{18}$), 35.1 ($C_{26}$), 34.5 ($C_{2'}$), 34.2 ($C_{16}$), 31.9 ($C_{2''}$), 30.6 ($C_{24}$), 27.5 ($C_{27}$), 25.9 (C(CH$_3$)$_3$), 23.5 (CH$_3$CONH), 20.2 ($C_{12a}$), 18.3 ($C_{6'}$), 17.1 ($C_{6''}$), 16.4 ($C_{24a}$), 15.1 ($C_{14a}$), 13.0 ($C_{26a}$), 12.1 ($C_{28}$); MS (FAB) 1184 (M+Li, 100). Anal. Calcd for $C_{64}H_{95}NO_{17}Si$: C, 65.23; H, 8.12; N, 1.19. Found: C, 65.48; H, 8.38; N, 1.11.

(C) 4a-Hydroxy-5-O-phenoxyacetyl-4"-epiacetylaminoavermectin $B_1$. A 250-mL round-bottom flask fitted with a magnetic stirring bar, septum and nitrogen inlet was charged with 4.40 g (3.73 mmol) of 4a-tert-butyldimethylsilyloxy-5-O-phenoxyacetyl-4"-epiacetylaminoavermectin $B_1$ in 36 mL of methanol. The clear solution was cooled to 0° C. and 35.5 mL of 2% p-toluenesulfonic acid in methanol was added dropwise. After stirring at 0° C. for 2 h, 70 mL of saturated aqueous sodium bicarbonate was added, followed by 50 mL of water. The resulting mixture was transferred to a separatory funnel and extracted with 4×70 mL of dichloromethane. The organic layers were combined, washed with 50 mL of saturated aqueous sodium bicarbonate and 50 mL of saturated aqueous sodium chloride. The organic phase was then dried over sodium sulfate, filtered, concentrated and chromatographed (7 cm×28 cm column, 96.25:3.75 dichloromethane:methanol) to afford 3.07 g (77%) of the alcohol as a foam: $R_f$=0.20 (94:6 dichloromethane:methanol);

$^1$H NMR δ7.28 (d, J=7.0, arom 2×H), 6.98 (t, J=7.0, aromH), 6.90 (d, J=7.0 2×aromH), 5.91 (brs, $H_3$), 5.86 (m, $H_9$), 5.80–5.68 (om, $H_5$, $H_{10}$, $H_{11}$, $H_{22}$), 5.55 (om, $H_{23}$, NH), 5.45–5.37 (om, $H_{19}$, $H_{1''}$), 4.98 (m, $H_{15}$), 4.75 (d, J=2.3, $H_{1'}$), 4.70 (s, OCH$_2$Ar), 4.60 (m, 2×$H_{8a}$), 4.42 (dm J=10.0, $H_{4''}$), 4.16 (d, J=6.1, $H_6$), 4.10 (om, $H_{4a}$, $H_{5''}$), 3.92 (brs, $H_{13}$), 3.90–3.78 (om, $H_{17}$, $H_{5'}$), 3.72–3.55 (om, $H_{3'}$, $H_{3''}$), 3.45 (d, J=10, $H_{25}$), 3.41 (s, OCH$_3$), 3.37 (om, OCH$_3$, $H_2$), 3.19 (t, J=9.0, $H_{4'}$), 2.50 (m, $H_{12}$), 2.32–2.15 (om, 2×$H_{16}$, $H_{24}$, $H_{2'eq}$), 2.04 (s, CH$_3$CO), 2.08–1.95 (om, $H_{20eq}$, $H_{2''eq}$), 1.78 (m, $H_{18eq}$), 1.68–1.40 (om, $H_{20}$, $H_{26}$, 2×$H_{27}$, $H_{2'}$, $H_{2''}$), 1.48 (s, 3×$H_{14a}$), 1.21 (d, J=6.2, 3×$H_{6'}$), 1.13 (d, J=6.9, 3×$H_{12a}$), 1.11 (d, J=6.6, 3×$H_{6''}$), 0.95–0.85 (om, 3×$H_{24a}$, 3×$H_{26a}$, 3×$H_{28}$, $H_{18ax}$); MS (FAB) 1086 (M+Na, 100). Anal. Calcd for $C_{58}H_{81}NO_{17}$: C, 65.46; H, 7.67; N, 1.32. Found: C, 65.68; H, 7.85; N, 0.94.

(D) 4a-Methoxyethoxymethoxy-4"-epiacetylaminoavermectin $B_1$. A 250-mL round-bottom flask fitted with a magnetic stirring bar, septum and nitrogen inlet was charged with 3.07 g (2.89 mmol) of 4a-hydroxy-5-O-phenoxyacetyl-4"-epiacetylaminoavermectin $B_1$ in 20 mL of acetonitrile. The clear solution was cooled to 0° C. and 3.40 g (15.9 mmol) of N,N,N',N'-tetramethyl-1,8-naphthalenediamine (proton sponge) was added in one portion, followed by a dropwise addition of 1.32 mL (1.44 g, 11.5 mmol) of 2-methoxyethoxymethyl chloride (MEM chloride). After stirring at 0° C. for 6 min, the reaction mixture was warmed to room temperature and stirred overnight. The amine-hydrochloride salt slowly precipitated from solution. After 14 h, 75 mL of saturated aqueous sodium bicarbonate was added, followed by 50 mL of water. The resulting mixture was transferred to a separatory funnel and extracted with 6×30 mL of ethyl acetate. The organic layers were combined, washed with 50 mL of saturated aqueous sodium bicarbonate and 50 mL of saturated aqueous sodium chloride. The organic phase was then dried over sodium sulfate, filtered, concentrated and chromatographed (7 cm×27 cm column, 96.75:3.25 dichloromethane:methanol) to afford 3.54 g (100+%) of the ether as a foam. This material was deprotected without further purification: $R_f=0.33$ (95:5 dichloromethane:methanol).

A 250-mL round-bottom flask fitted with a magnetic stirring bar, septum and nitrogen inlet was charged with 3.54 g (~2.89 mmol) of 4a-methoxyethoxymethoxy-5-O-phenoxyacetyl-4"-epiacetylaminoavermectin $B_1$ in 90 mL of dry tetrahydrofuran. The clear solution was cooled to −20° C. and 23 mL (1.0M in tetrahydrofuran, 23 mmol) of lithium tri-sec-butylborohydride (L-selectride) was added dropwise over 5 min via syringe. The reaction mixture was placed in a −20° C. freezer for 15 h. The reaction was stopped by the addition of 50 mL of water. The resulting mixture was transferred to a separatory funnel and extracted with 7×30 mL of dichloromethane. The organic layers were combined, washed with 2×50 mL of saturated aqueous sodium bicarbonate and 50 mL of saturated aqueous sodium chloride. The organic phase was then dried over sodium sulfate, filtered, concentrated and chromatographed (7 cm×27 cm column, 95.5:4.5 dichloromethane:methanol) to afford 1.11 g (38%) of the desired product as a foam and 1.43 g of mixed fractions. Chromatography (5 cm×27 cm column, 95.5:4.5 dichloromethane:methanol) of the mixed fractions provided an additional 0.63 g (21%) of material for a total of 1.74 g (59%). $R_f=0.13$ (95.5:4.5 dichloromethane:methanol).

$^1$H NMR δ5.85 (m, $H_9$), 5.78–5.68 (om, $H_{10}$, $H_{11}$, $H_{22}$, NH), 5.55 (om, $H_3$, $H_{23}$), 5.45–5.35 (om, $H_{19}$, $H_{1''}$), 4.98 (m, $H_{15}$), 4.80–4.75 (om, 2×$H_{8a}$, $H_{1'}$, $OCH_2O$), 4.52 (brt, J=~5, $H_5$), 4.42 (dm J=10.0, $H_{4''}$), 4.28 (brd, J=~10, $H_{4a}$), 4.12 (brd, J=~10, $H_{4a}$), 4.08 (s, 7-OH), 4.05 (m, $H_{5''}$), 3.98 (d, J=6.1, $H_6$), 3.92 (brs, $H_{13}$), 3.90–3.78 (om, $H_{17}$, $H_{5'}$), 3.75–3.50 (om, $H_{3'}$, $H_{3''}$, $OCH_2CH_2O$), 3.45 (d, J=10, $H_{25}$), 3.40 (s, $OCH_3$), 3.35 (s, $OCH_3$), 3.35 (om, $OCH_3$, $H_2$), 3.19 (t, J=9.0, $H_{4'}$), 2.85 (d, J=5, 5-OH), 2.50 (m, $H_{12}$), 2.32–2.15 (om, 2×$H_{16}$, $H_{24}$, $H_{2'eq}$), 2.04 (s, $CH_3CO$), 2.08–1.95 (om, $H_{20eq}$, $H_{2''eq}$), 1.78–1.40 (om, $H_{18eq}$, $H_{20}$, $H_{26}$, 2×$H_{27}$, $H_{2'}$, $H_{2''}$), 1.45 (s, 3×$H_{14a}$), 1.21 (d, J=6.2, 3×$H_{6'}$), 1.13 (d, J=6.9, 3×$H_{12a}$), 1.11 (d, J=6.6, 3×$H_{6''}$), 0.95–0.85 (om, 3×$H_{24a}$, 3×$H_{26a}$, 3×$H_{28}$, $H_{18ax}$); MS (FAB) 1040 (M+Na, 100), 1018 (M+H, 40).

EXAMPLE 8

4"-epiacetylamino-4a-hydroxy-avermectin $B_1$-5-ketoxime

A 25-mL round-bottom flask fitted with a magnetic stirring bar, septum and nitrogen inlet was charged with 170 mg (163 μmol) of 4a-tert-butyldimethylsilyloxy-4"-epiacetylaminoavermectin $B_1$ (see Example 7) and 3 mL of dry N,N-dimethylformamide. To the resulting pale yellow solution was added 125 mg (326 μmol) of 98% pyridinium dichromate (PDC). After 1.5 h at room temperature, 5 mL of water and 5 mL of ethyl acetate were added. The resulting mixture was poured into a separatory funnel containing 30 mL of water and extracted with 4×30 mL of ethyl acetate. The organic layers were combined, washed with 4×50 mL of water, dried over sodium sulfate, filtered and concentrated to provide 164 mg (97%) of the corresponding ketone that was used without further purification. $R_f=0.29$ (95:5 dichloromethane:methanol).

A 50-mL round-bottom flask fitted with a magnetic stirring bar, septum and nitrogen inlet was charged with 164 mg (157 μmol) of 4"-epiacetylamino-4a-tert-butyl-dimethylsilyloxy-5-oxoavermectin $B_1$ in 5 mL of dry ethyl acetate. To the resulting clear solution was added 400 mL (400 μmol, 1M in diethyl ether) of zinc chloride followed by 100 mL (86 mg, 820 μmol) of O-(trimethylsilyl)hydroxylamine at room temperature. The reaction mixture was stirred at room temperature for 2 h, then quenched by the addition of 10 mL of saturated aqueous sodium bicarbonate. The reaction mixture was transferred to a separatory funnel and extracted with 4×20 mL of ethyl acetate. The organic layers were combined, washed with 3×50 mL of saturated aqueous sodium bicarbonate and 50 mL of saturated aqueous sodium chloride, dried over sodium sulfate, filtered and concentrated. The crude silyl ether-oxime was then dissolved in 8 mL of dry methanol in a 50-mL round-bottom flask fitted with a magnetic stirring bar, septum and nitrogen inlet. The resulting clear solution was cooled to 0° C. and 3 mL of 1% p-toluenesulfonic acid in methanol was added dropwise. The reaction was quenched after 1 h by addition of 10 mL of saturated aqueous sodium bicarbonate. The reaction mixture was transferred to a separatory funnel and 25 mL of water was added. The mixture was extracted with 4×30 mL of dichloromethane. The combined organic layers were washed with 100 mL of saturated aqueous sodium bicarbonate and 50 mL of saturated aqueous sodium chloride, dried over sodium sulfate, filtered through Celite, concentrated and purified by preparative TLC (2×1.5 mm thick plates, 2 elutions with 93:7 dichloromethane:methanol) to provide 70 mg (47%) of 4"-epiacetylamino-4a-hydroxy-avermectin $B_1$-5-ketoxime as a foam: $R_f=0.14$ (94:6 dichloromethane:methanol). MS (FAB) 966 (M+Na, 100), 944 (M+H, 65).

EXAMPLE 9

4"-Morpholinylcarbonylhydrazonyl-4a-hydroxy-avermectin $B_1$ (A) 4a-Hydroxyavermectin $B_1$. Using the same procedure as Example 1, 4a-hydroxyavermectin $B_1$ was prepared from avermectin $B_1$: yield 2.04 g (50%): $R_f=0.17$ (94:6 dichloromethane:methanol); MS (FAB) 895 (M+Li, 100). Anal. Calcd for $C_{48}H_{72}O_{15}$: C, 64.84; H, 8.16. Found: C, 65.05; H, 7.91.

(B) 4a,5-O-bis(tert-butyldimethylsilyl)avermectin $B_1$. A 100-mL round-bottom flask fitted with a magnetic stirring bar, septum and nitrogen inlet was charged with 820 mg (922 μmol) of 4a-hydroxyavermectin $B_1$ in 8.2 mL of N,N-dimethyl formamide. To the clear solution was added 314 mg (4.61 mmol) of imidazole and 359 mg (2.31 mmol) of tert-butylchlorodimethylsilane. After stirring at 20° C. for 2.67 h, the reaction mixture was quenched by the addition of 30 mL of water followed by 20 mL of ethyl acetate. The layers were separated and the aqueous phase was extracted with 4×40 mL of ethyl acetate. The organic layers were combined, washed with 100 mL of water, dried over sodium sulfate, filtered, concentrated and chromatographed (4 cm×24 cm column, 97.5:2.5 dichloromethane:methanol) to afford 712 mg (70%) of 4a,5-O-bis(tert-butyldimethylsilyl)avermectin $B_1$ as a foam: $R_f$=0.20 (97.5:2.5 dichloromethane:methanol).

(C) 4"-[2-((Morpholin-4-yl)carbonyl)hydrazon-1-yl]-4a-hydroxyavermectin $B_1$. To a solution of 74 mL (108 mg, 850 μmol) of oxalyl chloride in 7 mL of dichloromethane at −78° C. in a 100-mL round-bottom flask fitted with a thermometer, magnetic stirring bar, septum, and nitrogen inlet was added dropwise 86 μl (95 mg, 1.2 mmol) of dimethyl sulfoxide. After 15 min, a solution of 592 mg (530 μmol) of 4a,5-O-bis(tert-butyldimethylsilyl)avermectin $B_1$ in 4 mL of dichloromethane was added via syringe over 17 min. After 45 min at −78° C., 554 μl (402 mg, 3.97 mmol) of triethylamine was added over 2 min. The reaction was allowed to warm to room temperature, stirred at room temperature for 40 min, then partitioned between 40 mL of dichloromethane and 50 mL of water. The aqueous layer was extracted with 4×40 mL of dichloromethane. The organic layers were combined, washed with 100 mL of saturated aqueous sodium bicarbonate and 100 mL of saturated sodium chloride. The combined organic layers were dried over sodium sulfate, filtered and concentrated to afford 602 mg (100+%) of 4a,5-O-bis(tert-butyldimethylsilyl)-4"-oxoavermectin $B_1$ as a foam: $R_f$=0.54 (96.5:3.5 dichloromethane:methanol).

A 100-mL round-bottom flask fitted with a magnetic stirring bar, septum and nitrogen inlet was charged with 557 mg (500 μmol) of 4a,5-O-bis(tert-butyldimethylsilyl)-4"-oxoavermectin $B_1$ in 5 mL of methanol. The clear solution was cooled to 0° C. and 5.4 mL of 2% p-toluenesulfonic acid in methanol was added dropwise. After stirring at 0° C. for 2 h, 20 mL of saturated aqueous sodium bicarbonate was added, followed by 20 mL of water. The resulting mixture was transferred to a separatory funnel and extracted with 4×40 mL of dichloromethane. The organic layers were combined, washed with 200 mL of saturated aqueous sodium bicarbonate and 200 mL of saturated aqueous sodium chloride. The organic phase was then dried over sodium sulfate, filtered, concentrated and chromatographed (4 cm×27 cm column, 94.5:5.5 dichloromethane:methanol) to afford 382 mg (86%) of 4a-hydroxy-4"-oxoavermectin $B_1$ as a foam: $R_f$=0.29 (94:6 dichloromethane:methanol).

A 100-mL round-bottom flask fitted with a magnetic stirring bar, septum and nitrogen inlet was charged with 382 mg (431 μmol) of 4a-hydroxy-4"-oxoavermectin $B_1$ and 375 mg (2.58 mmol) of 4-morpholinecarbonyl hydrazine in 15 mL of methanol. The clear solution was stirred at room temperature and 4 mL of 2% p-toluenesulfonic acid in methanol was added dropwise. After stirring at room temperature for 1 h, 20 mL of saturated aqueous sodium bicarbonate was added, followed by 20 mL of water. The resulting mixture was transferred to a separatory funnel and extracted with 4×40 mL of dichloromethane. The organic layers were combined, washed with 200 mL of saturated aqueous sodium bicarbonate and 200 mL of saturated aqueous sodium chloride. The organic phase was then dried over sodium sulfate, filtered, concentrated and chromatographed (4 cm×27 cm column, 94:6 dichloromethane:methanol) to afford 300 mg (69%) of 4"-[2-((Morpholin-4-yl)carbonyl)hydrazon-1-yl]-4a-hydroxyavermectin $B_1$ as a foam: $R_f$=0.29 (94:6 dichloromethane:methanol). MS (FAB): 1035 (M+Na, 100).

EXAMPLE 10

4"-O-(Methoxyethoxymethyl)-4a-hydroxyavermectin $B_1$

A 5-mL flask fitted with a magnetic stirring bar was charged with 120 mg (107 μmol) of 4a,5-O-bis(tert-butyldimethylsilyl)avermectin $B_1$ (see Example 9) in 2 mL of acetonitrile. The clear solution was cooled to 0° C. and 46 mg (220 μmol) of N,N,N',N'-tetramethyl-1,8-naphthalenediamine (proton sponge) was added in one portion, followed by a dropwise addition of 18 μL (20 mg, 160 μmol) of 2-methoxyethoxymethyl chloride (MEM chloride). After stirring at 0° C. for 15 min, the reaction mixture was warmed to room temperature and stirred overnight. The amine-hydrochloride salt slowly precipitated from solution. After 18.5 h, a second charge of 55 mg (260 μmol) of N,N,N',N'-tetramethyl-1,8-naphthalenediamine (proton sponge) was added in one portion, followed by a dropwise addition of 20 μL (22 mg, 180 μmol) of 2-methoxyethoxymethyl chloride (MEM chloride). After 40 h, 2 mL of saturated aqueous sodium bicarbonate was added and the resulting mixture was transferred to a separatory funnel containing 10 mL of water and extracted with 3×20 mL of ethyl acetate. The organic layers were combined, washed with 20 mL of 1.0M aqueous sodium hydrogen sulfate and 20 mL of saturated aqueous sodium chloride. The organic phase was then dried over sodium sulfate, filtered, and concentrated to provide 127 mg of crude 4a,5-bis-O-tert-butyldimethylsilyloxy-4"-O-methoxyethoxymethylavermectin $B_1$ that was deprotected without further purification: $R_f$=0.43 (96.5:3.5 dichloromethane:methanol).

A 100-mL round-bottom flask fitted with a magnetic stirring bar, septum and nitrogen inlet was charged with 127 mg (105 μmol) of 4a,5-bis-O-tert-butyldimethylsilyloxy-4"-O-methoxyethoxymethylavermectin $B_1$ in 2 mL of methanol. The clear solution was cooled to 0° C. and 1.2 mL of 2% p-toluenesulfonic acid in methanol was added dropwise. After stirring at 0° C. for 3.5 h, 20 mL of saturated aqueous sodium bicarbonate was added, followed by 10 mL of water. The resulting mixture was transferred to a separatory funnel and extracted with 4×40 mL of dichloromethane. The organic layers were combined, washed with 20 mL of saturated aqueous sodium bicarbonate and 50 mL of saturated aqueous sodium chloride. The organic phase was then dried over sodium sulfate, filtered, concentrated and purified by preparative TLC (1.5 mm plate, 93:7 dichloromethane:methanol) to afford 86 mg (84%) of 4"-O-(methoxyethoxymethyl)-4a-hydroxyavermectin $B_1$ as a foam: $R_f$=0.32 (93:7 dichloromethane:methanol). MS (FAB): 999 (M+Na, 100).

EXAMPLE 11

4a-Hydroxy-4",4a-bis-O-(Methoxyethoxymethyl)avermectin $B_1$ (A) 5-O-tert-Butyldimethylsilyl-4a-hydroxyavermectin $B_1$. A 20-mL polypropylene vial fitted with a magnetic stirring bar was charged with 230 mg (206 μmol) of 4a,5-bis-O-tert-butyldimethylsilyloxyavermectin $B_1$ in 9.5 mL of distilled tetrahydrofuran. The clear solution was cooled to 0° C. and ~0.7 mL of hydrogen fluoride-pyridine solution (the solution consists of 25 g of commercial hydrogen-fluoride-pyridine diluted with 27.5 mL of tetrahydrofuran and 12.5 mL of pyridine) was added dropwise. After warming to room temperature and stirring for 3 h, 5 mL of pyridine followed by 5 mL of saturated aqueous potassium carbonate was added. The resulting mixture was transferred to a separatory funnel and extracted with 6×15 mL of ethyl acetate. The organic layers were combined and washed with 2×50 mL of saturated aqueous potassium carbonate. The organic phase was then dried over sodium sulfate, filtered, concentrated and chromatographed (2 cm×31.5 cm column, 96.75:3.25 dichloromethane:methanol) to afford 169 mg (90%) of 5-O-tert-Butyldimethylsilyl-4a-hydroxyavermectin $B_1$ as a foam: $R_f$=0.16 (96.75:3.25 dichloromethane:methanol).

(B) 4a-Hydroxy-4'',4a-bis-O-(Methoxyethoxymethyl)avermectin $B_1$. A 50-mL flask fitted with a magnetic stirring bar was charged with 169 mg (168 μmol) of 5-O-tert-Butyldimethylsilyl-4a-hydroxyavermectin $B_1$ in 3 mL of acetonitrile. The clear solution was cooled to 0° C. and 290 mg (1.35 mmol) of N,N,N',N'-tetramethyl-1,8-naphthalenediamine (proton sponge) was added in one portion, followed by a dropwise addition of 115 μL (125 mg, 1.01 mmol) of 2-methoxyethoxymethyl chloride (MEM chloride). After stirring at 0° C. for 10 min, the reaction mixture was warmed to room temperature and stirred overnight. The amine-hydrochloride salt slowly precipitated from solution. After 18.5 h, 10 mL of saturated aqueous sodium bicarbonate was added and the resulting mixture was transferred to a separatory funnel containing 10 mL of water and extracted with 7×10 mL of ethyl acetate. The organic layers were combined, washed with 2×50 mL of saturated aqueous sodium bicarbonate, 20 mL of 1.0 M aqueous sodium hydrogen sulfate and 20 mL of saturated aqueous sodium chloride. The organic phase was then dried over sodium sulfate, filtered, and concentrated and purified by preparative TLC (2×1.5 mm thick plates, 96.15:3.85 dichloromethane:methanol) to provide 154 mg (78%) of 4'',4a-bis-O-(methoxyethoxymethyl)-5-O-tert-butyldimethylsilylavermectin $B_1$: $R_f$=0.27 (96:4 dichloromethane:methanol).

A 20-mL polypropylene vial fitted with a magnetic stirring bar was charged with 154 mg (131 μmol) of 4a-hydroxy-4'',4a-bis-O-(methoxyethoxymethyl)-5-O-tert-butyldimethylsilyloxyavermectin $B_1$ in 5 mL of distilled tetrahydrofuran. The clear solution was cooled to 0° C. and ~0.6 mL of hydrogen fluoridepyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 16.7 h, 3 mL of pyridine followed by 5 mL of saturated aqueous potassium carbonate and 5 mL of water were added. The resulting mixture was transferred to a separatory funnel and extracted with 6×15 mL of ethyl acetate. The organic layers were combined and washed with 2×40 mL of saturated aqueous potassium carbonate. The organic phase was then dried over sodium sulfate, filtered, concentrated, concentrated from 10 mL of toluene, and purified by preparative TLC (2×1.0 mm thick plates, 94:6 dichloromethane:methanol) to afford 60 mg (43%) of 4a-hydroxy-4'',4a-bis-O-(methoxyethoxymethyl)-avermectin $B_1$ as a foam: $R_f$=0.28 (95:5 dichloromethane:methanol). MS (FAB): 1071 (M+Li, 100).

EXAMPLE 12

4a-Benzoyloxy-4''-O-methoxyethoxymethylavermectin $B_1$

A 25-mL round-bottom flask fitted with a magnetic stirring bar, septum and nitrogen inlet was charged with 130 mg (130 μmol) of 5-O-tert-butyldimethylsilyl-4a-hydroxyavermectin $B_1$ (see Example 11), 68 mg (260 μmol) of $Ph_3P$ and 64 mg (520 μmol) of benzoic acid in 3 mL of dichloromethane. To the resulting clear solution was added 41 μL (45 mg, 260 μmol) of diethyl azodicarboxylate at room temperature over 5 min. The resulting solution was stirred at room temperature for 25 min. The reaction was quenched by the addition of 15 mL of saturated aqueous sodium bicarbonate and poured into a separatory funnel containing 15 mL of dichloromethane. The layers were separated and the aqueous layer was extracted with 2×15 mL of dichloromethane. The organic layers were combined, dried over sodium sulfate, filtered concentrated and purified by preparative TLC (3×1.5 mm thick plates, 95:5 dichloromethane:methanol) to provide 115 mg (80%) of 4a-benzoyloxy-5-O-tert-butyldimethylsilylavermectin $B_1$ as a foam: $R_f$=0.38 (96:4 dichloromethane:methanol).

A 4-mL vial fitted with a magnetic stirring bar was charged with 123 mg (103 μmol) of 4a-benzoyl-5-O-tert-butyldimethylsilylavermectin $B_1$ in 1.5 mL of acetonitrile. The clear solution was cooled to 0° C. and 111 mg (518 μmol) of N,N,N',N'-tetramethyl-1,8-naphthalenediamine (proton sponge) was added in one portion, followed by a dropwise addition of 48 μL (52 mg, 410 μmol) of 2-methoxyethoxymethyl chloride (MEM chloride). After stirring at 0° C. for 2 min, the reaction mixture was warmed to room temperature and stirred overnight. The amine-hydrochloride salt slowly precipitated from solution. After 19 h, the reaction mixture was added to 10 mL of saturated aqueous sodium bicarbonate in a separatory funnel containing 10 mL of water and was extracted with 8×10 mL of ethyl acetate. The organic layers were combined, washed with 2×50 mL of saturated aqueous sodium bicarbonate, 20 mL of 1.0 M aqueous sodium hydrogen sulfate and 20 mL of saturated aqueous sodium chloride. The organic phase was then dried over sodium sulfate, filtered, and concentrated and purified by preparative TLC (2×1.0 mm thick plates, 96:4 dichloromethane:methanol) to provide 123 mg (99%) of 4a-hydroxy-4a-O-benzoyl-5-O-tert-butyldimethylsilyl-4''-O-methoxy-thoxymethylavermectin $B_1$: $R_f$=0.53 (96:4 dichloromethane:methanol).

A 20-mL polypropylene vial fitted with a magnetic stirring bar was charged with 154 mg (131 μmol) of 4a-O-benzoyl-5-O-tert-butyldimethylsilyl-4''-O-methoxyethoxymethylavermectin $B_1$ in 3 mL of distilled tetrahydrofuran. The clear solution was cooled to 0° C. and ~1 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 16.3 h, 2 mL of pyridine followed by 5 mL of saturated aqueous potassium carbonate and 5 mL of water were added. The resulting mixture was transferred to a separatory funnel and extracted with 7×15 mL of ethyl acetate. The organic layers were combined and washed with 3×20 mL of saturated aqueous potassium carbonate. The organic phase was then dried over sodium sulfate, filtered, concentrated, concentrated from 10 mL of toluene, and purified by preparative TLC (2×1.0 mm thick plates, 96:4 dichloromethane:methanol) to afford 100 mg (90%) of 4a-O-benzoyl-4''-O-methoxyethoxymethylavermectin $B_1$ as a foam: $R_f$=0.28 (95:5 dichloromethane:methanol). MS (FAB): 1087 (M+Li, 100).

EXAMPLE 13

4''-O-Methoxyethoxymethyl-4a-pyrrolecarboxyavermectin $B_1$

A 25-mL round-bottom flask fitted with a magnetic stirring bar, septum and nitrogen inlet was charged with 130 mg (130 μmol) of 5-O-tert-Butyldimethylsilyl-4a-hydroxyavermectin $B_1$ (see Example 11), 85 mg (320 μmol) of $Ph_3P$ and 72 mg (650 μmol) of 2-pyrrolecarboxylic acid in 3 mL of dichloromethane. To the resulting clear solution was added 51 μL (56 mg, 320 μmol) of diethyl azodicarboxylate at room temperature over 5 min. The reaction had not gone to completion, so an additional 34 mg (130 μmol) of $Ph_3P$ and 29 mg (260 μmol) of 2-pyrrolecarboxylic acid were added, followed by 20 μL (22 mg, 130 μmol) of diethyl azodicarboxylate added dropwise at room temperature. The resulting solution was stirred at room temperature for 45 min. The reaction was quenched by the addition of 15 mL of saturated aqueous sodium bicarbonate and poured into a separatory funnel containing 15 mL of dichloromethane. The layers were separated and the aqueous layer was extracted with 2×15 mL of dichloromethane. The organic layers were combined, dried over sodium sulfate, filtered concentrated and purified by preparative TLC (4×1.5 mm thick plates, 60:40 hexane:ethyl acetate) to provide 128 mg (90%) of 5-O-tert-butyldimethylsilyl-4a-pyrrolecarboxyavermectin $B_1$ as a foam: $R_f$=0.41 (67:33 hexane:ethyl acetate).

A 4-mL vial fitted with a magnetic stirring bar was charged with 128 mg (117 μmol) of 5-O-tert-butyldimethylsilyl-4a-pyrrolecarboxyavermectin $B_1$ in 1.5 mL of acetonitrile. The clear solution was cooled to 0° C. and 126 mg (585 μmol) of N,N,N',N'-tetramethyl-1,8-naphthalenediamine (proton sponge) was added in one portion, followed by a dropwise addition of 54 μL (59 mg, 480 μmol) of 2-methoxyethoxymethyl chloride (MEM chloride). After stirring at 0° C. for 3 min, the reaction mixture was warmed to room temperature and stirred overnight. The aminehydrochloride salt slowly precipitated from solution. After 19 h, a second charge of 25 mg (120 μmol) of N,N,N',N'-tetramethyl-1,8-naphthalenediamine (proton sponge) was added in one portion, followed by a dropwise addition of 15 μL (17 mg, 130 μmol) of 2-methoxyethoxymethyl chloride (MEM chloride). After 22 h, 2 mL of saturated aqueous sodium bicarbonate was added and the resulting mixture was transferred to a separatory funnel containing 10 mL of water and extracted with 5×10 ×10 mL of ethyl acetate. The organic layers were combined, washed with 40 mL of saturated aqueous sodium bicarbonate, 40 mL of 1.0 M aqueous sodium hydrogen sulfate and 40 mL of saturated aqueous sodium chloride. The organic phase was then dried over sodium sulfate, filtered, and concentrated and purified by preparative TLC (2×1.5 mm thick plates, 96:4 dichloromethane:methanol) to provide 120 mg (86%) of 5-O-tert-butyldimethylsilyl-4''-O-methoxyethoxymethyl-4a-pyrrolecarboxyavermectin $B_1$: $R_f$=0.43 (96:4 dichloromethane:methanol).

A 20-mL polypropylene vial fitted with a magnetic stirring bar was charged with 120 mg (102 μmol) of 5-O-tert-butyldimethylsilyl-4''-O-methoxyethoxymethyl-4a-pyrrolecarboxy-avermectin $B_1$ in 3 mL of distilled tetrahydrofuran. The clear solution was cooled to 0° C. and ~1 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 16.5 h, 2 mL of pyridine followed by 5 mL of saturated aqueous potassium carbonate and 5 mL of water were added. The resulting mixture was transferred to a separatory funnel and extracted with 5×15 mL of ethyl acetate. The organic layers were combined and washed with 3×40 mL of saturated aqueous potassium carbonate. The organic phase was then dried over sodium sulfate, filtered, concentrated, concentrated from 10 mL of toluene, and purified by preparative TLC (2×1.0 mm thick plates, 96:4 dichloromethane:methanol) to afford 79 mg (73%) of 4''-O-Methoxyethoxymethyl-4-a-pyrrolecarboxyavermectin $B_1$ as a foam: $R_f$=0.28 (95:5 dichloromethane:methanol). MS (FAB): 1076 (M+Li, 100).

EXAMPLE 14

4''-epi-N-Acetyl-N-methylamino-4a-hydroxyavermectin $B_1$ (A) 4''-epi-N-Acetyl-N-methylaminoavermectin $B_1$. A 250-mL round-bottom flask fitted with a magnetic stirring bar, septum and nitrogen inlet was charged with 5.00 g (5.54 mmol) of 4''-epi-N-methylaminoavermectin $B_1$ in 50 ml of ethyl acetate. To the resulting clear solution was added 800 μL (873 mg, 8.46 mmol) of acetic anhydride at room temperature. After stirring for 18 h, 10 mL of saturated aqueous sodium bicarbonate was added. The mixture was transferred to a separatory funnel and the layers were separated. The aqueous layer was washed with 30 mL of ethyl acetate. The organic layers were combined, dried over sodium sulfate, filtered, concentrated by rotary evaporation and chromatographed (4 cm×20 cm column, 97:3 dichloromethane:methanol) to provide 5.13 g (98%) of 4''-epi-N-acetyl-N-methylaminoavermectin $B_1$ as a foam: $R_f$=0.35 (93:7 dichloromethane/methanol).

(B) Using the same procedure as Example 1, 4''-epi-N-acetylamino-N-methyl-4a-hydroxyavermectin $B_1$ was prepared from 4''-epi-N-acetylamino-N-methylavermectin $B_1$: yield 404 mg (33%), isolated as a foam: $R_f$=0.19 (94:6 dichloromethane/methanol); MS (FAB) 966 (M+Na, 80), 344 (90), 312 (100), 221 (95).

EXAMPLE 15

4''-epi-Acetylamino-4a-(3-pyridinecarboxy)avermectin $B_1$

Using the procedure for Example 5 (substituting 3-pyridinecarboxylic acid for benzoic acid), 4''-epi-Acetylamino-4a-(3-pyridinecarboxy)avermectin $B_1$ was prepared from 4a-Hydroxy-4''-epiacetylaminoavermectin $B_1$: 145 mg (65%). $R_f$=0.31 (94:6 dichloromethane:methanol). MS (FAB) 1035 (M+1, 100), 1057 (M+Na, 40).

EXAMPLE 16

4"-epi-Acetylamino-4a-O-(4-dimethylaminobenzoyl)avermectin $B_1$

Using the procedure for Example 5 (substituting 3-(N,N-dimethylamino)-benzoic acid for benzoic acid), 4"-epi-Acetylamino-4a-O-(4-dimethylaminobenzoyl)avermectin $B_1$ was prepared from 4a-Hydroxy-4"-epiacetylaminoavermectin $B_1$: 186 mg (64%). $R_f=0.41$ (93:7 dichloromethane: methanol). MS (FAB) 1099 (M+Na, 100).

EXAMPLE 17

4"-O-Methoxyethoxymethyl-4a-methylthioavermectin $B_1$ (A) 5-O-tert-Butyldimethylsilyl-4a-hydroxy-4"-methoxyethoxymethylavermectin $B_1$ A 250-mL polypropylene bottle fitted with a magnetic stirring bar was charged with 2.4 g (1.99 mmol) of 4a, 5-O-bis(tert-butyldimethylsilyl)-4"-O-methoxyethoxymethylavermectin $B_1$ (see Example 10) in 92 mL of tetrahydrofuran. The clear solution was cooled to 0° C. and /6.6 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 2.5 h, 15 mL of pyridine followed by 15 mL of saturated aqueous potassium carbonate was added. The resulting mixture was transferred to a separatory funnel and extracted with 5×30 mL of ethyl acetate. The organic layers were combined and washed with 3×50 mL of saturated aqueous potassium carbonate. The organic phase was then dried over sodium sulfate, filtered, concentrated and chromatographed (6 cm×34 cm column, 97.5:2.5 dichloromethane:methanol) to afford 1.72 g (79%) of 5-O-tert-butyldimethylsilyl-4a-hydroxy-4"-methoxyethoxymethylavermectin $B_1$ as a foam: $R_f=0.24$ (75:25 hexane:acetone).

(B) 5-O-tert-Butyldimethylsilyl-4"-O-methoxyethoxymethyl-4a-methylthioavermectin $B_1$ A 25-mL round-bottom flask fitted with a magnetic stirring bar, septum and nitrogen inlet was charged with 100 mg (0.092 mmol) of 5-O-tert-butyldimethylsilyl-4a-hydroxy-4"-methoxyethoxymethylavermectin $B_1$ in 2 mL of dichloromethane. To the resulting clear solution was added 230 μL (185 mg, 0.917 mmol) of tributylphosphine followed by 42 μL (44 mg, 0.46 mmol) of dimethyl disulfide at room temperature. After 5 h, 115 μL (93 mg, 0.461 mmol) of tributylphosphine followed by 21 μL (22 mg, 0.23 mmol) of dimethyl disulfide was added at room temperature. The resulting solution was stirred at room temperature for 22 h. The reaction mixture was then quenched by the addition of 5 mL of saturated aqueous sodium bicarbonate. The mixture was transferred to a separatory funnel and extracted 5×4 mL of dichloromethane. The combined organic layers were washed with 2×5 mL of saturated aqueous sodium bicarbonate, washed with 10 mL of saturated aqueous sodium chloride, dried over sodium sulfate, filtered, concentrated by rotary evaporation and purified by preparative TLC (4×1.5 mm thick plates), 97.5:2.5 dichloromethane:methanol) to provide 57 mg (55%) of 5-O-tert-butyldimethylsilyl-4"-O-methoxyethoxymethyl-4a-methylthioavermectin $B_1$ as a foam: $R_f=0.28$ (97.5:2.5 dichloromethane/methanol).

(C) .4"-O-Methoxyethoxymethyl-4a-methylthioavermectin $B_1$

A 20-mL polypropylene vial fitted with a magnetic stirring bar was charged with 57 mg (51 μmol) of 5-O-tert-butyldimethylsilyl-4"-O-methoxyethoxymethyl-4a-methylthioavermectin $B_1$ in 3 mL of tetrahydrofuran. The clear solution was cooled to 0° C. and about 1 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 16 h, 5 mL of pyridine followed by 5 mL of saturated aqueous potassium carbonate was added. The resulting mixture was transferred to a separatory funnel and extracted with 5×6 mL of ethyl acetate. The organic layers were combined and washed with 3×20 mL of saturated aqueous potassium carbonate. The organic phase was then dried over sodium sulfate, filtered, concentrated and purified by preparative TLC (1.0 mm thick plate), 75:25 hexane-:acetone) to afford 48 mg (94%) of 4"-O-methoxyethoxymethyl-4a-methylthioavermectin $B_1$ as a foam: $R_f=0.23$ (75:25 hexane:acetone).

EXAMPLE 18

4a-Benzyloxymethoxy-4"-O-methoxyethoxymethylavermectin $B_1$ (A) 5-O-tert-Butyldimethylsilyl-4"-O-methoxyethoxymethyl-4a-trimethylsiloxy-7-O-trimethylsilylavermectin $B_1$ A 25-mL round-bottom flask fitted with a magnetic stirring bar, septum and nitrogen inlet was charged with 60 mg (0.055 mmol) of 5-O-tert-butyldimethylsilyl-4a-hydroxy-4"-methoxyethoxymethylavermectin $B_1$ (see Example 17) in 1 mL of N,N-dimethylformamide. To the resulting clear solution was added 1.0 mL (0.97 g, 3.8 mmol) of bis(trimethylsilyl) trifluoroacetamide. The resulting mixture was warmed to 40° C. and stirred for 17 h. The reaction mixture was then quenched by the addition of 10 mL of water. The mixture was transferred to a separatory funnel and extracted 5×6 mL of ethyl acetate. The combined organic layers were washed with 3×20 mL of saturated aqueous sodium chloride, dried over sodium sulfate, filtered, concentrated by rotary evaporation and purified by preparative TLC (1.5 mm thick plate), 75:25 hexane:acetone) to provide 54 mg (80%) of 5-O-tert-butyldimethylsilyl-4"-O-methoxyethoxymethyl-4a-trimethylsiloxy-7-O-trimethylsilylavermectin $B_1$ as a foam: $R_f=0.49$ (75:25 hexane:acetone).

(B) 5-O-tert-Butyldimethylsilyl-4a-hydroxy-4"-O-methoxyethoxymethyl-7-O-trimethylsilylavermectin $B_1$ A 25-mL round-bottom flask fitted with a magnetic stirring bar was charged with 54 mg (0.044 mmol) of 5-O-tert-butyldimethylsilyl-4"-O-methoxyethoxymethyl-4a-trimethylsiloxy-7-O-trimethylsilylavermectin $B_1$ in 1.3 mL of tetrahydrofuran, 0.4 mL of water and 0.2 mL of glacial acetic acid. The clear solution was stirred at room temperature for 8 min, then quenched by the addition of 10 mL of saturated aqueous sodium bicarbonate. The resulting mixture was transferred to a separatory funnel and extracted with 6×5 mL of ethyl acetate. The organic layers were combined and washed with 3×20 mL of saturated aqueous sodium bicarbonate and 20 mL of saturated aqueous sodium chloride. The organic phase was then dried over sodium sulfate, filtered, concentrated and purified by preparative TLC (1.5 mm thick plate), 75:25 hexane:acetone) to afford 50 mg (98%) of 5-O-tert-butyldimethylsilyl-4a-hydroxy-4''-O-methoxyethoxymethyl-7-O-trimethylsilylavermectin $B_1$ as a foam: $R_f$=0.38 (75:25 hexane:acetone).

(C) 4a-Benzyloxymethoxy-5-O-tert-butyldimethylsilyl-4''-O-methoxyethoxymethyl-7-O-trimethylsilylavermectin $B_1$ A 25-mL round-bottom flask fitted with a magnetic stirring bar, septum and nitrogen inlet was charged with 50 mg (0.043 mmol) of 5-O-tert-butyldimethylsilyl-4a-hydroxy-4''-O-methoxyethoxymethyl-7-O-trimethylsilylavermectin $B_1$ in 1.5 mL of acetonitrile. The clear solution was cooled to 0° C. and 92 mg (0.44 mmol) of N,N,N',N'-tetramethyl-1,8-naphthalenediamine was added in one portion, followed by a dropwise addition of 48 μL (54 mg, 0.34 mmol) of chloromethyl benzyl ether (BOM chloride). After stirring at 0° C. for 3 min, the reaction mixture was warmed to room temperature and stirred. The amine-hydrochloride salt slowly precipitated from solution. After 7 h, 10 mL of saturated aqueous sodium bicarbonate was added, followed by 5 mL of water. The resulting mixture was transferred to a separatory funnel and extracted with 6×10 mL of ethyl acetate. The organic layers were combined, washed with 30 mL of saturated aqueous sodium bicarbonate, 30 mL of 1N sodium hydrogen sulfate and 30 mL of saturated aqueous sodium chloride. The organic phase was then dried over sodium sulfate, filtered, concentrated and purified by preparative TLC (2×1.0 mm thick plates), 75:25 hexane:acetone) to afford 7 mg (14%) of 4a-benzyloxymethoxy-5-O-tert-butyldimethylsilyl-4''-O-methoxyethoxymethylavermectin $B_1$, 6 mg (13%) of 4a-benzyloxymethoxy-4''-O-methoxyethoxymethylavermectin $B_1$, 7 mg (13%) of 4a-benzyloxymethoxy-5-O-tert-butyldimethylsilyl-4''-O-methoxyethoxymethyl-7-O-trimethylsilylavermectin $B_1$ the ether as a foam: $R_f$=0.35 (75:25 hexane:acetone).

(D) 4a-Benzyloxymethoxy-4''-O-methoxyethoxymethylavermectin $B_1$

The two silylated derivatives were combined and desilylated with hydrogen fluoride-pyridine solution as described in Example 17 to afford a total of 15 mg of 4a-benzyloxymethoxy-4''-O-methoxyethoxymethylavermectin $B_1$ as a foam: $R_f$=0.34 (67:33 hexane:acetone); MS (FAB) 1119 (M+Na, 100), 973 (70), 550 (70), 369 (80), 329 (95).

EXAMPLE 19

13-O-Methoxyethoxymethyl-4a-methoxyethoxymethoxy-22,23-dihydroavermectin $B_1$ aglycone (A) 4a-tert-Butyldimethylsiloxy-5-O-tert-butyldimethylsilyl-13-O-methoxyethoxymethyl-22,23-dihydroavermectin $B_1$ aglycone.

A 25-mL round-bottom flask fitted with a magnetic stirring bar, septum and nitrogen inlet was charged with 400 mg (567 μmol) of 13-O-methoxyethoxymethyl-4a-hydroxy-22,23-dihydroavermectin $B_1$ aglycone (Example 3) in 4 mL of N,N-dimethylformamide. To the clear solution was added 231 mg (3.40 mmol) of imidazole and 256 mg (1.70 mmol) of tert-butylchlorodimethylsilane. After stirring at 20° C. for 3.75 h, the reaction mixture was quenched by the addition of 10 mL of water followed by 10 mL of ethyl acetate. The layers were separated and the aqueous phase was extracted with 4×10 mL of ethyl acetate. The organic layers were combined, washed with 50 mL of water, dried over sodium sulfate, filtered, concentrated and chromatographed (4 cm×27 cm column, 8:1 hexane:ethyl acetate) to afford 468 mg (88%) of 4a-tert-butyldimethylsiloxy-5-O-tert-butyldimethylsilyl-13-O-methoxyethoxymethyl-22,23-dihydroavermectin $B_1$ aglycone as a foam: $R_f$=0.42 (4:1 hexane:ethyl acetate).

(B) 5-O-tert-Butyldimethylsilyl-4a-hydroxy-13-O-methoxyethoxymethyl-22,23-dihydroavermectin $B_1$ aglycone A 50-mL polypropylene vial fitted with a magnetic stirring bar was charged with 468 mg (0.510 mmol) of 4a-tert-butyldimethylsiloxy-5-O-tert-butyldimethylsilyl-13-O-methoxyethoxymethyl-22,23-dihydroavermectin $B_1$ aglycone in 25 mL of tetrahydrofuran. The clear solution was cooled to 0° C. and 1.7 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 3.7 h, 5 mL of pyridine followed by 15 mL of saturated aqueous potassium carbonate was added. The resulting mixture was transferred to a separatory funnel and extracted with 4×15 mL of ethyl acetate. The organic layers were combined and washed with 3×20 mL of saturated aqueous potassium carbonate. The organic phase was then dried over sodium sulfate, filtered, concentrated and chromatographed (4 cm×27 cm column, 3:1 hexane:ethyl acetate) to afford 404 mg (98%) of 5-O-tert-butyldimethylsilyl-4a-hydroxy-13-O-methoxyethoxymethyl-22,23-dihydroavermectin $B_1$ aglycone as a foam: $R_f$=0.35 (3:1 heaxane:acetone).

(C) 5-O-tert-Butyldimethylsilyl-4a-methoxyethoxymethoxy-13-O-methoxyethoxymethyl-22,23-dihydroavermectin $B_1$ aglycone A 25-mL round-bottom flask fitted with a magnetic stirring bar, septum and nitrogen inlet was charged with 404 mg (0.502 mmol) of 5-O-tert-butyldimethylsilyl-4a-hydroxy-13-O-methoxyethoxymethyl-22,23-dihydroavermectin $B_1$ aglycone in 8 mL of acetonitrile. The clear solution was cooled to 0° C. and 539 mg (2.51 mmol) of N,N,N',N'-tetramethyl-1,8-naphthalenediamine was added in one portion, followed by a dropwise addition of 188 μL (205 mg, 1.51 mmol) of methoxyethoxymethyl chloride (MEM chloride). After stirring at 0° C. for 3 min, the reaction mixture was warmed to room temperature and stirred. The amine-hydrochloride salt slowly precipitated from solution. After 20 h, 10 mL of saturated aqueous sodium bicarbonate was added, followed by 5 mL of water. The resulting mixture was transferred to a separatory funnel and extracted with 6×10 mL of ethyl acetate. The organic layers were combined, washed with 30 mL of saturated aqueous sodium bicarbonte, 30 mL of 1N sodium hydrogen sulfate and 30 mL of saturated aqueous sodium chloride. The organic phase was then dried over sodium sulfate, filtered, concentrated and chromatographed (4 cm×30 cm column, 75:25 hexane:acetone) to afford 288 mg (64%) of 5-O-tert-butyldimethylsilyl-4a-methoxyethoxymethoxy-13-O-methoxyethoxymethyl-22,23-dihydroavermectin $B_1$ aglycone as a foam: $R_f$=0.44 (2:1 hexane:acetone).

(D) 13-O-Methoxyethoxymethyl-4a-methoxyethoxymethoxy-22,23-dihydroavermectin $B_1$ aglycone A 20-mL polypropylene vial fitted with a magnetic stirring bar was charged with 288 mg (322 μmol) of 5-O-tert-butyldimethylsilyl-4a-methoxyethoxymethoxy-13-O-methoxyethoxymethyl-22,23-dihydroavermectin $B_1$ aglycone in 6 mL of tetrahydrofuran. The clear solution was cooled to 0° C. and 1.6 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 16 h, 5 mL of pyridine followed by 5 mL of saturated aqueous potassium carbonate was added. The resulting mixture was transferred to a separatory funnel and extracted with 5×15 mL of ethyl acetate. The organic layers were combined and washed with 4×10 mL of saturated aqueous potassium carbonate. The organic phase was then dried over sodium sulfate, filtered, concentrated and chromatographed (3 cm×23 cm, 1:3 hexane:ethyl acetate) to afford 220 mg (88%) of 13-O-methoxyethoxymethyl-4a-methoxyethoxymethoxy-22,23-dihydroavermectin $B_1$ aglycone as a foam: $R_f$=0.23 (1:3 hexane:ethyl acetate); MS (FAB) 786 (M+Li, 100), 686 (20).

EXAMPLE 20

4″epi-N-Acetyl-N-methylamino-4a-methoxyethoxymethoxyavermectin $B_1$

Using the same procedures (steps A–D) provided for Example 19, 170 mg of 4″epi-N-acetyl-N-methylamino-4a-methoxyethoxymethoxyavermectin $B_1$ was prepared from 295 mg of 4″-epi-N-acetyl-N-methylamino-4a-hydroxyavermectin (Example 14). Data for 4″epi-N-acetyl-N-methylamino-4a-methoxyethoxymethoxyavermectin $B_1$: $R_f$=0.23 (96:4 dichloromethane:methanol); MS (FAB) 1038 (M+Li, 85), 939 (50), 200 (100), 161 (62).

EXAMPLE 21

4″-epi-N-Acetylamino-4a-benzyloxymethoxyavermectin $B_1$

4″-epi-N-Acetylamino-5-O-tert-butyldimethylsilyl-4a-hydroxyavermectin $B_1$

Using the same procedures (steps A–B) provided for Example 19, 309 mg of 4″-epi-N-acetylamino-5-O-tert-butyldimethylsilyl-4a-hydroxyavermectin $B_1$ was prepared from 344 mg of 4″-epi-N-acetylamino-4a-hydroxyavermectin (Example 1).

(C) 4″-epi-N-Acetylamino-5-O-tert-butyldimethylsilyl-4a-hydroxy-7-O-trimethylsilylavermectin $B_1$ A 25-mL round-bottom flask fitted with a magnetic stirring bar, septum and nitrogen inlet was charged with 309 mg (0.296 mmol) of 4″-epi-N-acetylamino-5-O-tert-butyldimethylsilyl-4a-hydroxyavermectin $B_1$ in 3 mL of N,N-dimethylformamide. To the resulting clear solution was added 6.0 mL (5.8 g, 22 mmol) of bis(trimethylsilyl) trifluoroacetamide. The resulting mixture was warmed to 40° C. and stirred for 17 h. The reaction mixture was then quenched by the addition of 10 mL of water. The mixture was transferred to a separatory funnel and extracted 6×10 mL of ethyl acetate. The combined organic layers were washed with 2×30 mL of saturated aqueous sodium chloride, dried over sodium sulfate, filtered, and concentrated by rotary evaporation to provide 369 mg (110%) of crude product. The crude product was used without purification in the next reaction.

A 25-mL round-bottom flask fitted with a magnetic stirring bar was charged with 369 mg (0.296 mmol) of 4″-epi-N-acetylamino-5-O-tert-butyldimethylsilyl-4a-trimethylsiloxy-7-O-trimethylsilylavermectin $B_1$ in 8 mL of tetrahydrofuran, 2.4 mL of water and 1.2 mL of glacial acetic acid. The clear solution was stirred at room temperature for 8 min, then quenched by the addition of 10 mL of saturated aqueous sodium bicarbonate. The resulting mixture was transferred to a separatory funnel and extracted with 6×15 mL of ethyl acetate. The organic layers were combined and washed with 2×20 mL of saturated aqueous sodium bicarbonate and 20 mL of saturated aqueous sodium chloride. The organic phase was then dried over sodium sulfate, filtered, concentrated and chromatographed (3 cm×25 cm column, 2.5:1 hexane:acetone) to afford 300 mg (91%) of 4″-epi-N-acetylamino-5-O-tert-butyldimethylsilyl-4a-hydroxy-7-O-trimethylsilylavermectin $B_1$ as a foam: $R_f$=0.28 (2.5:1 hexane:acetone).

(D) 4″-epi-N-Acetylamino-4a-benzyloxymethoxy-5-O-tert-butyldimethylsilyl-7-O-trimethylsilylavermectin $B_1$ A 25-mL round-bottom flask fitted with a magnetic stirring bar, septum and nitrogen inlet was charged with 136 mg (0.110 mmol) of 4″-epi-N-acetylamino-5-O-tert-butyldimethylsilyl-4a-hydroxy-7-O-trimethylsilylavermectin $B_1$ in 2.5 mL of acetonitrile. The clear solution was cooled to 0° C. and 118 mg (0.550 mmol) of N,N,N′,N′-tetramethyl-1,8-naphthalenediamine was added in one portion, followed by a dropwise addition of 61 μL (69 mg, 0.44 mmol) of chloromethyl benzyl ether (BOM chloride). After stirring at 0° C. for 3 min, the reaction mixutre was warmed to room temperature and stirred. After stirring for 5 h, 118 mg (0.550 mmol) of N,N,N′,N′-tetramethyl-1,8-naphthalenediamine was added in one portion, followed by a dropwise addition of 61 μL (69 mg, 0.44 mmol) of chloromethyl benzyl ether (BOM chloride). The amine-hydrochloride salt slowly precipitated from solution. After 22 h, 10 mL of saturated aqueous sodium bicarbonate was added, followed by 5 mL of water. The resulting mixture was transferred to a separatory funnel and extracted with 4×10 mL of ethyl acetate. The organic layers were combined, washed with 30 mL of saturated aqueous sodium bicarbonate, 2×30 mL of 1N sodium hydrogen sulfate and 30 mL of saturated aqueous sodium chloride. The organic phase was then dried over sodium sulfate, filtered, concentrated and purified by preparative TLC (2×1.5 mm thick plates), 60:40 hexane:acetone) to afford 137 mg (90%) of 4″-epi-N-acetylamino-4a-benzyloxymethoxy-5-O-tert-butyldimethylsilyl-7-O-trimethylsilylavermectin $B_1$ as a foam: $R_f$=0.32 (60:40 hexane:acetone).

(E) 4″-epi-N-Acetylamino-4a-benzyloxymethoxyavermectin $B_1$

A 20-mL polypropylene vial fitted with a magnetic stirring bar was charged with 137 mg (111 μmol) of 4″-epi-N-acetylamino-4a-benzyloxymethoxy-5-O-tert-butyldimethylsilyl-7-O-trimethylsilylavermectin $B_1$ in 3 mL of tetrahydrofuran. The clear solution was cooled to 0° C. and 1 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 15 h, 5 mL of pyridine followed by 5 mL of saturated aqueous potassium carbonate was added. The resulting mixture was transferred to a separatory funnel and extracted with 5×10 mL of ethyl acetate. The organic layers were combined and washed with 3×15 mL of saturated aqueous potassium carbonate. The organic phase was then dried over sodium sulfate, filtered, concentrated and purified by preparative TLC (2×1.0 mm thick plates), 1:1 hexane:acetone) to afford 95 mg (82%) of 4"-epi-N-acetylamino-4a-benzyloxymethoxyavermectin $B_1$ as a foam: $R_f = 0.27$ (1:1 hexane:acetone); MS (FAB) 1056 (M+Li, 100), 925 (40).

EXAMPLE 22

4"-epi-N-Acetylamino-4a-benzyloxyavermectin $B_1$ (A) 4"-epi-N-Acetylamino-5-O-tert-butyldimethylsilyl-4a-benzyloxyavermectin $B_1$ A 25-mL round-bottom flask fitted with a magnetic stirring bar, septum and nitrogen inlet was charged with 100 mg (95.8 μmol) of 4"-epi-N-acetylamino-5-O-tert-butyldimethylsilyl-4a-hydroxyavermectin $B_1$ (see Example 21) in 0.3 mL of carbon tetrachloride and 0.2 mL of cyclohexane. To the resulting clear solution was added 72 μL (98 mg, 383 μmol) of benzyl trichloroacetimidate followed by 96 μL (9.6 μmol, 0.1M in diethyl ether) of triflic acid at room temperature over 5 min. The resulting solution was stirred at room temperature for 15 min. After stirring at room temperature for 4 hr, 96 μL (9.6 μmol, 0.1M in diethyl ether) of triflic acid was added again. After 72 h, the reaction was quenched by the addition of 15 mL of saturated aqueous sodium bicarbonate and poured into a separatory funnel containing 15 mL of ethyl acetate. The layers were separated and the aqueous layer was extracted with 2×15 mL of ethyl acetate. The organic layers were combined, dried over sodium sulfate, filtered concentrated and purified by preparative TLC (3×1.0 mm thick plates), 94:6 dichloromethane:methanol) to provide 32 mg (30%) of 4"-epi-N-acetylamino-5-O-tert-butyldimethylsilyl-4a-benzyloxyavermectin $B_1$ as a foam: $R_f = 0.44$ (94:6 dichloromethane:methanol).

(B) 4"-epi-N-Acetylamino-4a-benzyloxyavermectin $B_1$

Using procedure E from Example 21, 32 mg (0.028 mmol) of 4"-epi-N-acetylamino-5-O-tert-butyldimethylsilyl-4a-benzyloxyavermectin $B_1$ was converted to 17 mg (59%) of 4"-epi-N-Acetylamino-4a-benzyloxyavermectin $B_1$: $R_f = 0.31$ (94:6 dichloromethane:methanol); MS (FAB) 1026 (M+Li, 65), 336 (100), 313 (90).

EXAMPLE 23

4"-epi-N-Acetylamino-4a-(1-tetrahydropyran)oxyavermectin $B_1$ (A) 4"-epi-N-Acetylamino-4a-(1-tetrahydropyran)oxy-5-O-phenoxyacetylavermectin $B_1$ A 50-mL round-bottom flask fitted with a magnetic stirring bar, septum and nitrogen inlet was charged with 564 mg (530 μmol) of 4a-hydroxy-5-O-phenoxyacetyl-4"-epi-N-acetylaminoavermectin $B_1$ (from Example 7, step C) in 7.3 mL of dihydropyran. To the resulting clear solution was added 5 mg (20 μmol) of pyridinium p-toluenesulfonate at room temperature. The resulting solution was stirred at room temperature for 40 min. The reaction was quenched by the addition of 15 mL of saturated aqueous sodium bicarbonate and poured into a separatory funnel containing 15 mL of ethyl acetate. The layers were separated and the aqueous layer was extracted with 4×10 mL of ethyl acetate. The organic layers were combined, washed with 2×40 mL of saturated aqueous sodium bicarbonate, washed with 30 mL of saturated aqueous sodium chloride, dried over sodium sulfate, filtered concentrated and chromatographed (4 cm×30 cm column, 60:40 hexane:acetone) to provide 386 mg (64%) of 4"-epi-N-acetylamino-4a-(1-tetrahydropyranyl)oxy-5-O-tert-phenoxyacetylavermectin $B_1$ as a foam: $R_f = 0.16$ (60:40 hexane:acetone).

(B) 4"-epi-N-Acetylamino-4a-(1-tetrahydropyranyl)oxyavermectin $B_1$

A 25-mL round-bottom flask fitted with a magnetic stirring bar, septum and nitrogen inlet was charged with 336 mg (293 μmol) of 4"-epi-N-acetylamino-4a-(1-tetrahydropyranyl)oxy-5-O-phenoxyacetylavermectin $B_1$ in 3.5 mL of methanol. The resulting green solution was cooled to −20° C. and 134 μL (146 μmol, 1.09M in methanol) of sodium methoxide was added dropwise. The resulting solution was stirred at −20° C. for 2 h, then the reaction was quenched by the addition of 5 mL of dichloromethane followed by 15 mL of saturated aqueous ammonium chloride. The resulting solution was poured into a separatory funnel containing 10 mL of dichloromethane. The layers were separated and the aqueous layer was extracted with 5×10 mL of dichloromethane. The organic layers were combined and washed with 2×20 mL of saturated aqueous ammonium chloride, 20 mL of saturated aqueous sodium bicarbonate. The organic phase was then dried over sodium sulfate, filtered concentrated and chromatographed (3 cm×30 cm column, 97:3 dichloromethane:methanol) to provide 243 mg (82%) of 4"-epi-N-acetylamino-4a-(1-tetrahydropyranyl)oxyavermectin $B_1$ as a foam: $R_f = 0.15$ (97:3 dichloromethane:methanol); MS (FAB) 1021 (M+Li, 100).

EXAMPLE 24

4a-Methoxyethoxymethoxy-4"-epiacetylamino-22,23-dihydroavermectin $B_1$

A 100-mL round-bottom flask fitted with a magnetic stirring bar, septum and gas inlet was charged with 1.00 g (0.982 mmol) of 4a-methoxyethoxymethoxy-4"-epiacetylaminoavermectin $B_1$ (see Example 7) in 12 mL of toluene. To the clear solution was added 273 mg (0.295 mmol) of tris(triphenylphosphine)rhodium chloride (Wilkinson's catalyst). The system was evacuated (20 torr) and purged with nitrogen three times, followed by hydrogen three times. Finally, the system was put under a static balloon of hydrogen and stirred at room temperature. After stirring for 24 h, the reaction mixture was flushed with nitrogen, concentrated and chromatographed (6 cm×32 cm column, 96:4 dichloromethane:methanol) to afford 1.00 g (99%) of the the impure product. Purification in two batches by preparative HPLC (2 cm×50 cm Whatman Partisil-10 ODS column, 254 nm, 82:18 methanol:water, 10 mL/min) provided pure 4a-methoxyethoxymethoxy-4"-epiacetylamino-22,23-dihydroavermectin $B_1$: $R_f = 0.16$ (96.5:3.5 dichloromethane:methanol); MS (FAB) 1027 (M+Li, 100).

EXAMPLE 25

4a-Hydroxy-22,23-dihydroavermectin $B_1$ monosaccharide

Using the same procedure as Example 1, 4a-hydroxy-22,23-dihydroavermectin $B_1$ monosaccharide was prepared: yield 490 mg (48%), isolated as a foam: $R_f = 0.28$ (98:2 dichloromethane/methanol); $^1$H NMR/5.86 (m, $H_9$), 5.75–5.65 (om, $H_3$, $H_{10}$, $H_{11}$), 5.35 (m, $H_{19}$), 4.95 (m, $H_{15}$), 4.70 (d, J=3.2, $H_{1'}$), 4.68 (m, $H_{8a}$), 4.55 (br t, J=5.0, $H_5$), 4.30 (m, $H_{4a}$), 4.18 (s, 7-OH), 3.95 (d, J=6.3, $H_6$), 3.92 (brs, $H_{13}$), 3.88–3.72 (m, $H_{17}$), 3.71–3.50 (om, $H_{3'}$, $H_{5'}$), 3.48 (s, $OCH_3$), 3.32 (m, $H_2$), 3.20 (obs, OH), 3.18 (brq, J=7.0, H$_4$'), 2.72 (d, J=5, OH), 2.60 (brs, OH), 2.50 (m, H$_{12}$), 2.32-2.15 (om, 2×H$_{16}$, H$_{24}$, H$_{2'eq}$), 2.05-1.95 (om, H$_{20eq}$), 1.75 (m, H$_{18eq}$), 1.65-1.40 (om, H$_{20}$, 2×H$_{22}$, 2×H$_{23}$, H$_{26}$, 2×H$_{27}$, H$_{2'}$), 1.48 (s, 3×H$_{14a}$), 1.21 (d, J=6.2, 3×H$_{6'}$), 1.15 (d, J=6.9, 3×H$_{12a}$), 0.95-0.85 (om, 3×H$_{24a}$, 3×H$_{26a}$, 3×H$_{28}$, H$_{18ax}$)

EXAMPLE 26

4a-Methoxyethoxymethoxy-4'-O-methoxyethoxymethyl-22,23-dihydroavermectin B$_1$ monosaccharide (A) 4a-tert-Butyldimethylsilyloxy-5-O-tert-butyldimethylsilyl-22,23-dihydroavermectin B$_1$ monosaccharide A 35-mL round-bottom flask fitted with a magnetic stirring bar, septum and nitrogen inlet was charged with 400 mg (535 μmol) of 4a-hydroxy-22,23-dihydroavermectin B$_1$ monosaccharide (Example 25) in 5 mL of N,N-dimethylformamide. To the clear solution was added 219 mg (3.21 mmol) of imidazole and 242 mg (1.61 mmol) of tert-butylchlorodimethylsilane. After stirring at 20° C. for 2.5 h, the reaction mixture was quenched by the addition of 10 mL of water followed by 10 mL of ethyl acetate. The layers were separated and the aqueous phase was extracted with 5×10 mL of ethyl acetate. The organic layers were combined, washed with 50 mL of water, dried over sodium sulfate, filtered, concentrated and chromatographed (4 cm×28 cm column, 4:1 hexane:ethyl acetate) to afford 85 mg (14%; R$_f$=0.68 (4:1 hexane:ethyl acetate)) of 4a-tert-butyldimethylsilyloxy-4',5-bis-O-tert-butyldimethylsilyl-22,23-dihydroavermectin B$_1$ monosaccharide and 306 mg (59%) of 4a-tert-butyldimethylsilyloxy-5-O-tert-butyldimethylsilyl-22,23-dihydroavermectin B$_1$ monosaccharide as a foam: R$_f$=0.22 (4:1 hexane:ethyl acetate).

(B) 5-O-tert-Butyldimethylsilyl-4a-hydroxy-22,23-dihydroavermectin B$_1$ monosaccharide A 50-mL polypropylene vial fitted with a magnetic stirring bar was charged with 306 mg (0.314 mmol) of 4a-tert-butyldimethylsilyloxy-5-O-tert-butyldimethylsilyl-22,23-dihydroavermectin B$_1$ monosaccharide in 15 mL of tetrahydrofuran. The clear solution was cooled to 0° C. and 1 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 3.75 h, 5 mL of pyridine followed by 5 mL of saturated aqueous potassium carbonate was added. The resulting mixture was transferred to a separatory funnel and extracted with 5×15 mL of ethyl acetate. The organic layers were combined and washed with 3×20 mL of saturated aqueous potassium carbonate. The organic phase was then dried over sodium sulfate, filtered, concentrated, concentrated from 2×30 mL of toluene and chromatographed (3 cm×29 cm column, 60:40 hexane:ethyl acetate) to afford 244 mg (90%) of 5-O-tert-butyldimethylsilyl-4-a-hydroxy-22,23-dihydroavermectin B$_1$ monosaccharide as a foam: R$_f$=0.23 (60:40 hexane:ethyl acetate).

(C) 5-O-tert-Butyldimethylsilyl-4a-methoxyethoxymethoxy-22,23-dihydroavermectin B$_1$ monosaccharide Procedure B from Example 11 was used to convert 244 mg of 5-O-tert-butyldimethylsilyl-4a-hydroxy-22,23-dihydroavermectin B$_1$ monosaccharide to 160 mg (61%) 4a-methoxyethoxymethoxy-4'-O-methoxyethoxymethyl-22,23-dihydroavermectin B$_1$ monosaccharide: R$_f$=0.28 (67:33 hexane:acetone); MS (FAB) 930 (M+Li, 100).

EXAMPLE 27

4a-Methoxyethoxymethoxy-22,23-dihydroavermectin B$_1$ monosaccharide

Using Procedures A and B from Example 11, 85 mg of 4a-tert-butyldimethylsilyloxy-4',5-bis-O-tert-butyldimethylsilyl-22,23-dihydroavermectin B$_1$ monosaccharide (Example 26) was converted to 29 mg (44%) of 4a-methoxyethoxymethoxy-22,23-dihydroavermectin B$_1$ monosaccharide: R$_f$=0.19 (67:33 hexane:acetone); MS (FAB) 842 (M+Li, 100).

EXAMPLE 28

4''-epi-Acetylamino-4a-methoxyavermectin B$_1$ (A) 4''-epi-Acetylamino-5-O-tert-butyldimethylsilyl-4a-methoxy-7-O-trimethylsilylavermectin B$_1$ A 5-mL round-bottom flask fitted with a magnetic stirring bar, septum and nitrogen inlet was charged with 50 mg (0.045 mmol) of 4''-epi-acetylamino-5-O-tert-butyldimethylsilyl-4a-hydroxy-7-O-trimethylsilylavermectin B$_1$ (see Example 21) in 0.5 mL of dichloromethane. The clear solution was cooled to 0° C. and 45 μL (38 mg, 0.20 mmol) of 2,6-di-tert-butylpyridine was added, followed by addition of 17 mg (0.11 mmol) of trimethyloxonium tetrafluoroborate in one portion. After stirring at 0° C. for 21 h, 3 mL of saturated aqueous sodium bicarbonate was added and the resulting mixture was transferred to a separatory funnel containing 5 mL of water and extracted with 5×6 mL of ethyl acetate. The organic layers were combined, washed with 3×10 mL of saturated aqueous sodium bicarbonate and 10 mL of saturated aqueous sodium chloride. The organic phase was then dried over sodium sulfate, filtered, and concentrated and purified by preparative TLC (2×1.0 mm thick plates), 67:33 hexane:acetone) to provide 30 mg (60%) of 4''-epi-acetylamino-5-O-tert-butyldimethylsilyl-4a-methoxy-7-O-trimethylsilylavermectin B$_1$: R$_f$=0.30 (67:33 hexane:acetone).

(B) 4''-epi-Acetylamino-4a-methoxyavermectin B$_1$

Using Procedure E from Example 21, 30 mg of 4''-epi-acetylamino-5-O-tert-butyldimethylsilyl-4a-methoxy-7-O-trimethylsilylavermectin B$_1$ was converted to 24 mg (96%) of 4''-epi-acetylamino-4a-methoxyavermectin B$_1$: R$_f$=0.40 (33:67 hexane:acetone); MS (FAB) 951 (M+Li, 100).

EXAMPLE 29

4''-epi-Acetylamino-4a-methylthiomethoxyavermectin B$_1$ (A) 4''-epi-Acetylamino-5-O-tert-butyldimethylsily-4a-methylthiomethoxy-7-O-trimethylsilylavermectin B$_1$ A 10-mL round-bottom flask fitted with a magnetic stirring bar, septum and nitrogen inlet was charged with 100 mg (0.090 mmol) of 4''-epi-acetylamino-5-O-tert-butyldimethylsilyl-4a-hydroxy-7-O-trimethylsilylavermectin B$_1$ (see Example 21) in 1 mL of dimethyl sulfoxide. To the resulting clear solution was added 845 μL (914 mg, 8.96 mmol) of acetic anhydride and 154 μL (162 mg, 2.69 mmol) of acetic acid at room temperature. The resulting solution was stirred at 40° C. for 5.25 h. The reaction was quenched by the addition of 5 mL of saturated aqueous sodium bicarbonate and poured into a separatory funnel containing 8 mL of ethyl acetate. The layers were separated and the aqueous layer was extracted with 3×8 mL of ethyl acetate. The organic layers were combined, dried over sodium sulfate, filtered concentrated and purified by preparative TLC (2×1.5 mm thick plates), 67:33 hexane:acetone) to provide 98 mg (93%) of impure (contaminated with 10% of $\Delta^{2,3}$ isomer) 4''-epi-acetylamino-5-O-tert-butyldimethylsilyl-4a-methylthiomethoxyavermectin $B_1$ as a foam: $R_f=0.64$ (50:50 hexane:acetone).

(B) 4''-epi-Acetylamino-4a-methylthiomethoxyavermectin $B_1$

A 20-mL polypropylene vial fitted with a magnetic stirring bar was charged with 98 mg (83 μmol) of the above mixture of 4''-epi-acetylamino-5-O-tert-butyldimethylsilyl-4a-methylthiomethoxy-7-O-trimethylsilylavermectin $B_1$ in 5 mL of tetrahydrofuran. The clear solution was cooled to 0° C. and about 1.5 mL of hydrogen fluoride-pyridine solution (the solution consists of 25 g of commmercial hydrogen fluoride-pyridine diluted with 27.5 mL of tetrahydrofuran and 12.5 mL of pyridine) was added dropwise. After warming to room temperature and stirring for 16 h, 2 mL of pyridine followed by 5 mL of saturated aqueous potassium carbonate and 5 mL of water were added. The resulting mixture was transferred to a separatory funnel and extracted with 7×15 mL of ethyl acetate. The organic layers were combined and washed with 3×20 mL of saturated aqueous potassium carbonate. The organic phase was then dried over sodium sulfate, filtered, concentrated, concentrated from 10 mL of toluene, and purified by preparative TLC (3×1000 μm plates, 50:50 hexane:acetone) to afford 70 mg of impure 4''-epi-acetylamino-4a-methylthiomethoxyavermectin $B_1$. Purification by preparative HPLC (2 cm×50 cm Whatman Partisil-10 ODS column, 254 nm, 82:18 methanol:water, 10 mL/min) provided pure 4''-epi-acetylamino-4a-methylthiomethoxyavermectin $B_1$: $R_f=0.30$ (50:50 hexane:acetone); MS (FAB) 997 (M+Li, 100).

EXAMPLE 30

4a-Methoxyethoxymethoxyavermectin $B_1$ (A) 4a-tert-Butyldimethylsiloxy-4'',5-bis-O-(tert-butyldimethylsilyl)avermectin $B_1$ A 25-mL round-bottom flask fitted with a magnetic stirring bar, septum and nitrogen inlet was charged with 524 mg (590 μmol) of 4a-hydroxyavermectin $B_1$ (see Example 9), 356 mg (2.36 mmol) of tert-butyldimethylsilyl chloride and 201 mg (2.95 mmol) of imidazole in 3 mL of N,N-dimethylformamide. The resulting solution was stirred at room temperature for 3 h. The reaction was quenched by the addition of 15 mL of 1 N aqueous sodium hydrogen sulfate and poured into a separatory funnel containing 15 mL of dichloromethane. The layers were separated and the aqueous layer was extracted with 2×15 mL of dichloromethane. The organic layers were combined, dried over sodium sulfate, filtered concentrated and chromatographed (3 cm×20 cm column, 6:1 hexane:ethyl acetate) to provide 581 mg (80%) of 4a-tert-butyldimethylsiloxy-4'',5-bis-O-(tert-butyldimethylsilyl)avermectin $B_1$ as a foam: $R_f=0.69$ (2:1 hexane:ethyl acetate).

(B) 4'',5-bis-O-(tert-Butyldimethylsilyl)-4a-hydroxyavermectin $B_1$

A 20-mL polypropylene vial fitted with a magnetic stirring bar was charged with 581 mg (472 μmol) of 4a-tert-butyldimethylsiloxy-4'',5-bis-O-(tert-butyldimethylsilyl)avermectin $B_1$ in 10 mL of tetrahydrofuran. The clear solution was cooled to 0° C. and 2 mL of hydrogen fluoride-pyridine solution (the solution consists of 25 g of commercial hydrogen fluoride-pyridine diluted with 27.5 mL of tetrahydrofuran and 12.5 mL of pyridine) was added dropwise. After warming to room temperature and stirring for 3.5 h, 5 mL of 1 N sodium hydrogen sulfate was added. The resulting mixture was transferred to a separatory funnel and extracted with 2×15 mL of dichloromethane. The organic layers were combined, dried over sodium sulfate, filtered, concentrated, and chromatographed (3 cm×20 cm column, 2:1 hexane:ethyl acetate) to afford 410 mg (78%) of 4'',5-bis-O-(tert-butyldimethylsilyl)-4a-hydroxyavermectin $B_1$ as a foam: $R_f=0.34$ (2:1 hexane:ethyl acetate).

(C) 4'',5-bis-O-(tert-Butyldimethylsilyl)-4a-methoxyethoxymethoxyavermectin $B_1$ Using procedure B from Example 11, 386 mg (0.345 mmol) of 4'',5-bis-O-(tert-butyldimethylsilyl)-4a-hydroxyavermectin $B_1$ was converted to 204 mg (60%) of 4a-methoxyethoxymethoxyavermectin $B_1$: $R_f=0.22$ (95:5 dichloromethane:methanol); MS (FAB): 983 (M+Li, 100).

EXAMPLE 31

4''-epi-Methylsulfonyl-4a-hydroxyavermectin $B_1$

Using the same procedure as Example 1, 421 mg of 4''-epi-methylsulfonyl-4a-hydroxyavermectin $B_1$ was prepared from 1.00 g 4''-epi-methylsulfonylavermectin $B_1$: yield (41%), isolated as a foam: $R_f=0.21$ (98:2 dichloromethane/methanol); MS (FAB) 957 (M+Li, 100).

EXAMPLE 32

4a-Methoxyethoxymethoxy-4''-epi-methylsulfonylavermectin $B_1$

Using Procedures A-D of Example 19, 400 mg of 4''-epi-methylsulfonyl-4a-hydroxyavermectin $B_1$ was converted to 166 mg (38%) of 4a-methoxyethoxymethoxy-4''-epi-methylsulfonylavermectin $B_1$: $R_f=0.28$ (ethyl acetate); MS (FAB) 1045 (M+Li, 100).

EXAMPLE 33

4a-Methoxyethoxymethoxy-22,23-dihydroavermectin $B_1$

Prepared from 4a-hydroxy-22,23-dihydroavermectin $B_1$ using the procedures from Example 1 followed by those from Example 30, to provide 4a-methoxyethoxymethoxy-22,23-dihydroavermectin $B_1$ with the expected physical properties.

EXAMPLE 34

4a-Methoxymethoxyavermectin $B_1$

Prepared from 4a-hydroxyavermectin $B_1$ using the procedures from Example 1 followed by those from Example 30, substituting chloromethyl methyl ether for methoxyethoxymethyl chloride in step C to provide 4a-methoxyethoxymethoxyavermectin $B_1$ with the expected physical properties.

EXAMPLE 35

4"-epi-Acetylamino-4a-methoxymethoxydihydroavermectin $B_1$

Prepared from 4"-epi-acetylamino-5-tert-butyldimethylsilyl-4a-hydroxyavermectin $B_1$ (Example 21) using Procedures C and D from Example 19, substituting chloromethyl methyl ether for methoxyethoxymethyl chloride in step C, to provide 4"-epiacetylamino-4a-methoxymethoxyavermectin $B_1$ with the expected physical properties.

EXAMPLE 36

4"-epi-N-Acetyl-N-methylamino-4a-methoxymethoxydihydroavermectin $B_1$

Prepared from 4"-epi-N-acetyl-N-methylamino -5-tert-butyldimethylsilyl-4a-hydroxyavermectin $B_1$ (Example 20) using Procedures C and D from Example 19, substituting chloromethyl methyl ether for methoxyethoxymethyl chloride in step C, to provide 4"-epi-N-acetyl-N-methylamino-4a-methoxymethoxyavermectin $B_1$ with the expected physical properties.

EXAMPLE 37

4a-O-Methoxyethoxymethoxymoxidectin.

(A) 4a-Hydroxymoxidectin. A 125-mL round-bottom flask fitted with a magnetic stirring bar, septum and nitrogen inlet is charged with 6.0 g (9.38 mmol) of moxidectin in 45 mL of dichloromethane. To the resulting clear solution is added 520 mg (4.69 mmol) of selenium dioxide followed by 2.09 mL (1.88 g, 18.8 mmol) of 90% tert-butylhydroperoxide at room temperature. The resulting solution is stirred at room temperature for 5 h. The reaction mixture is then concentrated by rotary evaporation and chromatographed with a dichloromethane:methanol solvent to provide 4a-hydroxymoxidectin with the expected physical properties, including NMR and mass spectra.

(B) 4a-tert-Butyldimethylsiloxy-5-O-tert-butyldimethylsilylmoxidectin. A 25-mL round-bottom flask fitted with a magnetic stirring bar, septum and nitrogen inlet is charged with 372 mg (567 µmol) of 4a-hydroxymoxidectin in 4 mL of N,N-dimethylformamide. To the clear solution is added 231 mg (3.40 mmol) of imidazole and 256 mg (1.70 mmol) of tert-butylchlorodimethylsilane. After stirring at 20° C. for 3.75 h, the reaction mixture is quenched by the addition of 10 mL of water followed by 10 mL of ethyl acetate. The organic layers are combined, washed with 50 mL of water, dried over sodium sulfate, filtered, concentrated and chromatographed with a hexane:ethyl acetate solvent mixture to afford 4a-tert-butyldimethylsiloxy-5-O-tert-butyldimethylsilylmoxidectin with the expected physical properties, including NMR and mass spectra.

(C) 5-O-tert-Butyldimethylsiyl-4a-hydroxymoxidectin. A 50-mL polypropylene vial fitted with a magnetic stirring bar is charged with 400 mg (0.452 mmol) of 4a-tert-butyldimethylsiloxy-5-O-tert-butyldimethylsilymoxidectin in 25 mL of tetrahydrofuran. The clear solution is cooled to 0° C. and ~1.7 mL of hydrogen fluoride-pyridine solution (the solution consists of 25 g of commercial hydrogen fluoride-pyridine diluted with 27.5 mL of tetrahydrofuran and 12.5 mL of pyridine) is added dropwise. After warming to room temperature and stirring for 3.7 h, 5 mL of pyridine followed by 15 mL of saturated aqueous potassium carbonate is added. The resulting mixture is transferred to a separatory funnel and extracted with 4×15 mL of ethyl acetate. The organic layers are combined and washed with 3×20 mL of saturated aqueous potassium carbonate. The organic phase is then dried over sodium sulfate, filtered, concentrated and chromatographed with a hexane:ethyl acetate solvent mixture to afford 5-O-tert-butyldimethylsilyl-4a-hydroxymoxidectin with the expected physical properties, including NMR and mass spectra.

(D) 5-O-tert-Butyldimethylsilyl-4a-methoxyethoxymethoxymoxidectin. A 25-mL round-bottom flask fitted with a magnetic stirring bar, septum and nitrogen inlet is charged with 300 mg (0.3909 mmol) of 5-O-tert-butyldimethylsilyl-4a-hydroxymoxidectin in 5 mL of acetonitrile. The clear solution is cooled to 0° C. and 322 mg (1.50 mmol) of N,N,N',N'-tetramethyl-1,8-naphthalenediamine is added in one portion, followed by a dropwise addition of 94 µL (100 mg, 0.76 mmol) of methoxyethoxymethyl chloride (MEM chloride). After stirring at 0° C. for 3 min, the reaction mixture is warmed to room temperature and stirred. The amine-hydrochloride salt slowly precipitates from solution. After 20 h, 10 mL of saturated aqueous sodium bicarbonate is added, followed by 5 mL of water. The resulting mixture is transferred to a separatory funnel and extracted with 6×10 mL of ethyl acetate. The organic layers are combined, washed with 30 mL of saturated aqueous sodium bicarbonate, 30 mL of 1 N sodium hydrogen sulfate and 30 mL of saturated aqueous sodium chloride. The organic phase is then dried over sodium sulfate, filtered, concentrated and chromatographed with a hexane:acetone solvent mixture to afford 5-O-tert-butyldimethylsilyl-4a-methoxyethoxymethoxy moxidectin with the expected physical properties, including NMR and mass spectra.

(E) 4a-O-Methoxyethoxymethoxymoxidectin. A 20-mL polypropylene vial fitted with a magnetic stirring bar is charged with 230 mg (268 µmol) of 5-O-tert-butyldimethylsiyl-4a-methoxyethoxymethoxymoxidectin in 6 mL oftetrahydrofuran. The clear solution is cooled to 0° C. and ~1.6 mL of hydrogen fluoride-pyridine solution (the solution consists of 25 g of commercial hydrogen fluoride-pyridine diluted with 27.5 mL of tetrahydrofuran and 12.5 mL of pyridine) is added dropwise. After warming to room temperature and stirring for 16 h, 5 mL of pyridine followed by 5 mL of saturated aqueous potassium carbonate is added. The resulting mixture is transferred to a separatory funnel and extracted with 5×15 mL of ethyl acetate. The organic layers are combined and washed with 4×10 mL of saturated aqueous potassium carbonate. The organic phase is then dried over sodium sulfate, filtered, concentrated and chromatographed with a hexane:ethyl acetate solvent mixture to afford 4a-O-methoxyethoxymethylmoxidectin with the expected physical properties, including NMR and mass spectra.

What is claimed is:

1. A compound having the formula

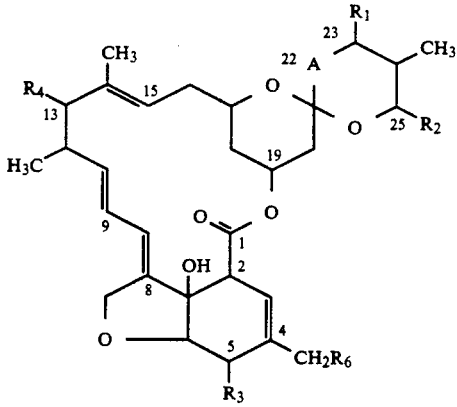

where
A is a 22,23 single bond or a double bond;
$R_1$ is hydrogen, hydroxy, oxo, oximino or methoxyimino, provided that $R_1$ is hydroxy only when A is a single bond;
$R_2$ is $C_1$-$C_8$ alkyl, or $C_2$-$C_8$ alkenyl or a $C_3$-$C_8$ cycloalkyl;
$R_3$ is hydroxy, methoxy, oxo or hydroximino;
$R_4$ is

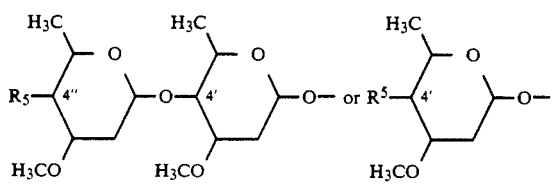

where $R_5$ hydroxy, oxo, amino, $C_1$-$C_8$ mono- or dialkyl amino, $C_1$-$C_8$-alkanoyl amino, N-$C_1$-$C_8$ alkyl-N-$C_1$-$C_8$ alkanoyl amino, ($C_1$-$C_8$ alkoxy)$_n$ where n is 1 to 4, $C_1$-$C_8$ alkylthio, $C_1$-$C_8$ alkylsulfinyl or $C_1$-$C_8$ alkylsulfonyl; and $R_6$ is hydroxy, $C_1$-$C_8$ alkanoyloxy, benzoyloxy, di $C_1$-$C_8$ alkylamino benzoyloxy, ($C_1$-$C_8$ alkoxy)$_n$ where n is 1-4, $C_1$-$C_8$ alkylthio, $C_1$-$C_8$ alkylthioalkoxy or oleandrosyloxy, provided that $R_6$ is hydroxy, $C_1$-$C_8$ alkanoyloxy or benzoyloxy, only when $R_5$ is other than hydroxy.

2. A compound of claim 1 where:
A is a 22,23-single bond or double bond and $R_1$ is hydrogen;
$R_2$ is $C_3$-$C_6$ alkyl or $C_5$-$C_6$ cycloalkyl;
$R_3$ is hydroxy or hydroximino;
$R_4$ is

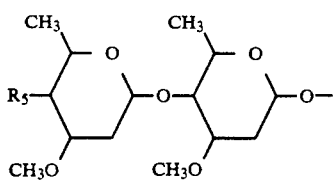

where $R_5$ is hydroxy, $C_2$-$C_4$ alkanoyl amino, N-$C_1$-$C_4$-alkyl-N-$C_1$-$C_4$ alkanoyl amino, ($C_1$-$C_4$ alkoxy)$_n$ where n is 1 to 4; and $R_6$ is hydroxy, $C_2$-$C_4$ alkanoyloxy, benzoyloxy, or ($C_1$-$C_4$ alkoxy)$_n$ where n is 1-4.

3. A compound of claim 2 where:

A is a 22,23-single bond or double bond and $R_1$ is hydrogen;
$R_2$ is $C_3$-$C_6$ branched alkyl or $C_6$ cycloalkyl;
$R_3$ is hydroxy;
$R_4$ is

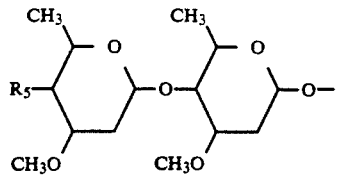

where $R_5$ is $C_2$-$C_4$ alkanoyl amino or N-$C_1$-$C_2$ alkyl-N-$C_2$-$C_3$ alkanyolamino; and $R_6$ is hydroxy, acetoxy, benzoyloxy, or ($C_1$-$C_2$ alkoxy)$_n$ where n is 1-3.

4. A compound of claim 3 where:
A is a 22,23-single bond or double bond and $R_1$ is hydrogen;
$R_2$ is isopropyl or sec-butyl;
$R_3$ is hydroxy;
$R_4$ is

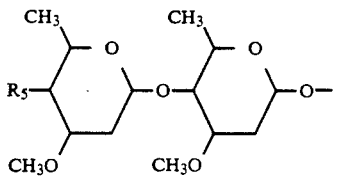

where $R_5$ is N-acetyl amino or N-methyl-N-acetyl amino; and
$R_6$ is hydroxy, acetoxy, benzoyloxy, or methoxy ethoxy methoxy.

5. A compound of claim 1 which is 4a-methoxyethoxymethoxy-4''-epi acetyl amino avermectin B1 or 4a-methoxyethoxymethoxy-22,23-dihydro-4''-epiacetylamino avermectin B1 or 4a-methoxyethoxy methoxy-4''-epi-(N-methyl-N-acetylamino) avermectin B1.

6. A compound of claim 1 which is 4''-epi-N-acetyl-N-methyl amino-4a-hydroxy avermectin B1.

7. A compound of claim 1 which is 4a-acetoxy-4''-epi-acetylamino avermectin B1 or 4a-methoxy-4''-epi-acetylamino avermectin B1.

8. A compound of claim 1 which is 4a-benzoyloxy-4''-epiacetyl-amino avermectin B1 or 4a-methoxyethoxymethoxy avermectin B1.

9. A compound of claim 1 which is 4a-methoxymethoxy avermectin B1, or 4a-methylthio methoxy avermectin B2.

10. A compound of claim 1 which is 4a-hydroxy-4''-epiacetyl-amino avermectin B1.

11. A compound of claim 1 which is 4a-hydroxy-4'',4a-bis-O-(methoxyethoxymethyl) avermectin $B_1$ or 4a,4''-bis-O-methyl-4a-hydroxy avermectin $B_1$.

12. A method for the treatment of parasitic infections in animals and plants which comprises orally, parenterally or topically treating such animals or topically treating such plants with an effective amount of compound of claim 1.

13. A composition useful for the oral, parenteral or topical treatment of parasitic infections in animals and the topical treatment of parasitic infections of plants which comprises an inert ingredient and an effective amount of a compound of claim 1.

* * * * *